(12) United States Patent
Hindrichs et al.

(10) Patent No.: US 9,492,277 B2
(45) Date of Patent: Nov. 15, 2016

(54) SOFT BODY TISSUE REMODELING METHODS AND APPARATUS

(75) Inventors: Paul J. Hindrichs, Plymouth, MN (US); Steven D. Kruse, St. Michael, MN (US); Todd A. Krinke, Rockford, MN (US); Michael P. Brenzel, St. Paul, MN (US); Kenton J. Zehr, Rochester, MN (US); Paul Thompson, Minnetonka, MN (US); Theodore P. Dale, Minneapolis, MN (US); David M. Costello, Waconia, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 1993 days.

(21) Appl. No.: 11/215,341

(22) Filed: Aug. 30, 2005

(65) Prior Publication Data

US 2007/0049942 A1 Mar. 1, 2007

(51) Int. Cl.
*A61F 2/24* (2006.01)
*A61B 17/128* (2006.01)
*A61B 17/04* (2006.01)

(52) U.S. Cl.
CPC ......... *A61F 2/2451* (2013.01); *A61B 17/1285* (2013.01); *A61B 2017/0409* (2013.01);
(Continued)

(58) Field of Classification Search
CPC ............ A61B 17/869; A61B 17/7032; A61B 17/7034; A61B 17/7022; A61B 17/8883; A61B 17/8891; A61B 17/8875; A61B 17/0409; A61B 2017/044; A61B 2017/0441; A61B 2017/0649; A61F 2/2451; B25B
(Continued)

(56) References Cited

U.S. PATENT DOCUMENTS 5,423,858 A * 6/1995 Bolanos et al. .............. 606/220
5,438,895 A * 8/1995 Bassell et al. ................ 81/451
(Continued)

FOREIGN PATENT DOCUMENTS

WO  WO 00/44313  8/2000
WO  WO 00/60995  10/2000
(Continued)

*Primary Examiner* — Alexander Orkin
(74) *Attorney, Agent, or Firm* — Marshall, Gerstein & Borun LLP

(57) ABSTRACT

Soft body tissue structure can be remodeled by shortening the distance between first and second portions of that tissue structure. First and second anchor structures are respectively implanted in the first and second portions of the tissue structure. These anchor structures are linked by a linking structure, the length of which between the anchor structures can be shortened to pull the tissue structure portions toward one another. Each of the anchor structures may include two screw structures that are driven into the associated tissue structure portion transverse to the linking structure and with a spacer between the two screws. The entire prosthesis can be implanted percutaneously if desired. An illustrative use of the prosthesis is to shorten the annulus of a patient's mitral valve, with at least a portion of the prosthesis implanted in the patient's coronary sinus.

28 Claims, 20 Drawing Sheets

(52) U.S. Cl.
CPC ..... *A61B 2017/0441* (2013.01); *A61B 2017/0488* (2013.01)

(58) Field of Classification Search
CPC ............... 15/004;B25B 15/005; B25B 15/007; B25B 15/008
USPC ................................. 606/151, 232; 623/2.11
See application file for complete search history.

(56) References Cited

U.S. PATENT DOCUMENTS

| | | | |
|---|---|---|---|
| 5,626,613 A | 5/1997 | Schmieding | |
| 5,716,358 A * | 2/1998 | Ochoa et al. | 606/62 |
| 5,824,011 A * | 10/1998 | Stone et al. | 606/232 |
| 5,849,004 A * | 12/1998 | Bramlet | 606/232 |
| 6,036,701 A * | 3/2000 | Rosenman | 606/151 |
| 6,106,526 A * | 8/2000 | Harms et al. | 606/278 |
| 6,182,664 B1 | 2/2001 | Cosgrove | |
| 6,210,432 B1 | 4/2001 | Solem et al. | |
| 6,296,656 B1 * | 10/2001 | Bolduc et al. | 606/213 |
| 6,402,781 B1 | 6/2002 | Langberg et al. | |
| 6,537,314 B2 | 3/2003 | Langberg et al. | |
| 6,569,198 B1 | 5/2003 | Wilson et al. | |
| 6,656,221 B2 | 12/2003 | Taylor et al. | |
| 6,663,633 B1 * | 12/2003 | Pierson, III | 606/148 |
| 6,676,702 B2 | 1/2004 | Mathis | |
| 6,702,826 B2 | 3/2004 | Liddicoat et al. | |
| 6,706,065 B2 | 3/2004 | Langberg et al. | |
| 6,709,456 B2 | 3/2004 | Langberg et al. | |
| 6,769,434 B2 | 8/2004 | Liddicoat et al. | |
| 6,790,231 B2 | 9/2004 | Liddicoat et al. | |
| 6,793,673 B2 | 9/2004 | Kowalsky et al. | |
| 6,797,001 B2 | 9/2004 | Mathis et al. | |
| 6,800,090 B2 | 10/2004 | Alferness et al. | |
| 6,810,882 B2 | 11/2004 | Langberg et al. | |
| 6,824,562 B2 | 11/2004 | Mathis et al. | |
| 8,231,639 B2 * | 7/2012 | Bolduc et al. | 606/142 |
| 2001/0018611 A1 | 8/2001 | Solem et al. | |
| 2001/0041821 A1 | 11/2001 | Wilk | |
| 2001/0044568 A1 | 11/2001 | Langberg et al. | |
| 2001/0047174 A1 * | 11/2001 | Donno et al. | 606/73 |
| 2001/0051815 A1 * | 12/2001 | Esplin | 606/232 |
| 2002/0016628 A1 | 2/2002 | Langberg et al. | |
| 2002/0042621 A1 | 4/2002 | Liddicoat et al. | |
| 2002/0042651 A1 | 4/2002 | Liddicoat et al. | |
| 2002/0095167 A1 | 7/2002 | Liddicoat et al. | |
| 2002/0103532 A1 | 8/2002 | Langberg et al. | |
| 2002/0103533 A1 | 8/2002 | Langberg et al. | |
| 2002/0156476 A1 * | 10/2002 | Wilford | 606/72 |
| 2002/0169502 A1 | 11/2002 | Mathis | |
| 2002/0183835 A1 | 12/2002 | Taylor et al. | |
| 2002/0183836 A1 | 12/2002 | Liddicoat et al. | |
| 2002/0183837 A1 | 12/2002 | Streeter et al. | |
| 2002/0183838 A1 | 12/2002 | Liddicoat et al. | |
| 2002/0183841 A1 | 12/2002 | Cohn et al. | |
| 2003/0013567 A1 | 1/2003 | Kern et al. | |
| 2003/0018358 A1 * | 1/2003 | Saadat | 606/232 |
| 2003/0069636 A1 | 4/2003 | Solem et al. | |
| 2003/0078465 A1 | 4/2003 | Pai et al. | |
| 2003/0078617 A1 * | 4/2003 | Schwartz et al. | 606/230 |
| 2003/0083538 A1 | 5/2003 | Adams et al. | |
| 2003/0105520 A1 | 6/2003 | Alferness et al. | |
| 2003/0130730 A1 | 7/2003 | Cohn et al. | |
| 2003/0130731 A1 | 7/2003 | Vidlund et al. | |
| 2003/0135267 A1 | 7/2003 | Solem et al. | |
| 2003/0144697 A1 | 7/2003 | Mathis et al. | |
| 2003/0171776 A1 | 9/2003 | Adams et al. | |
| 2003/0171806 A1 | 9/2003 | Mathis et al. | |
| 2003/0181928 A1 | 9/2003 | Vidlund et al. | |
| 2003/0212453 A1 | 11/2003 | Mathis et al. | |
| 2003/0225454 A1 | 12/2003 | Mathis et al. | |
| 2003/0229350 A1 * | 12/2003 | Kay | 606/72 |
| 2003/0236569 A1 | 12/2003 | Mathis et al. | |
| 2004/0010305 A1 | 1/2004 | Alferness et al. | |
| 2004/0019377 A1 | 1/2004 | Taylor et al. | |
| 2004/0034380 A1 | 2/2004 | Woolfson et al. | |
| 2004/0039443 A1 | 2/2004 | Solem et al. | |
| 2004/0059411 A1 * | 3/2004 | Strecker | 623/1.23 |
| 2004/0073302 A1 | 4/2004 | Rourke et al. | |
| 2004/0097973 A1 * | 5/2004 | Loshakove et al. | 606/144 |
| 2004/0102839 A1 | 5/2004 | Cohn et al. | |
| 2004/0102840 A1 | 5/2004 | Solem et al. | |
| 2004/0102841 A1 | 5/2004 | Langberg et al. | |
| 2004/0111095 A1 | 6/2004 | Gordon et al. | |
| 2004/0111101 A1 * | 6/2004 | Chin | 606/151 |
| 2004/0127980 A1 | 7/2004 | Kowalsky et al. | |
| 2004/0133220 A1 | 7/2004 | Lashinski et al. | |
| 2004/0133240 A1 | 7/2004 | Adams et al. | |
| 2004/0138683 A1 * | 7/2004 | Shelton et al. | 606/151 |
| 2004/0138744 A1 | 7/2004 | Lashinski et al. | |
| 2004/0153052 A1 | 8/2004 | Mathis | |
| 2004/0153147 A1 | 8/2004 | Mathis | |
| 2004/0158321 A1 | 8/2004 | Reuter et al. | |
| 2004/0176840 A1 | 9/2004 | Langberg et al. | |
| 2004/0186566 A1 | 9/2004 | Hindrichs et al. | |
| 2004/0193260 A1 | 9/2004 | Alferness et al. | |
| 2004/0210240 A1 | 10/2004 | Saint | |
| 2004/0220654 A1 | 11/2004 | Mathis et al. | |
| 2004/0236419 A1 | 11/2004 | Milo | |
| 2004/0243228 A1 | 12/2004 | Kowalsky et al. | |
| 2004/0249452 A1 | 12/2004 | Adams et al. | |
| 2004/0254600 A1 | 12/2004 | Zarbatany et al. | |
| 2005/0004667 A1 | 1/2005 | Swinford et al. | |
| 2006/0025784 A1 * | 2/2006 | Starksen et al. | 606/151 |
| 2009/0118776 A1 * | 5/2009 | Kelsch et al. | 606/325 |

FOREIGN PATENT DOCUMENTS

| | | |
|---|---|---|
| WO | WO 01/28455 A1 | 4/2001 |
| WO | WO 01/50985 | 7/2001 |
| WO | WO 01/54618 | 8/2001 |
| WO | WO 02/00099 | 1/2002 |
| WO | WO 02/01999 | 1/2002 |
| WO | WO 02/05888 | 1/2002 |
| WO | WO 02/19951 | 3/2002 |
| WO | WO 02/47539 | 6/2002 |
| WO | WO 02/053206 | 7/2002 |
| WO | WO 02/062263 | 8/2002 |
| WO | WO 02/062408 | 8/2002 |
| WO | WO 02/076284 | 10/2002 |
| WO | WO 02/078576 | 10/2002 |
| WO | WO 02/096275 | 12/2002 |
| WO | WO 03/015611 | 2/2003 |
| WO | WO 03/034947 | 5/2003 |
| WO | WO 03/055417 | 7/2003 |
| WO | WO 03/059198 | 7/2003 |
| WO | WO 03/088809 | 10/2003 |
| WO | WO 03/088873 | 10/2003 |
| WO | WO 2004/002290 | 1/2004 |
| WO | WO 2004/021893 | 3/2004 |
| WO | WO 2004/043293 | 5/2004 |

* cited by examiner

SOFT BODY TISSUE REMODELING METHODS AND APPARATUS

BACKGROUND OF THE INVENTION

This invention relates to medical devices and methods. More particularly, the invention relates to prostheses that can be used for such purposes as remodeling soft body tissue structures of a patient, and to instruments and methods that can be used for implanting such prostheses in a patient.

An example of a context in which this invention can be used is in a medical procedure that may be referred to as percutaneous mitral valve repair. Hindrichs et al. U.S. patent application Ser. No. 10/803,287, filed Mar. 17, 2004 (and hereby incorporated by reference herein in its entirety), shows this type of procedure, and methods and apparatus for performing it. An embodiment of this type of procedure includes percutaneously implanting a first anchor structure in the coronary sinus of the patient (e.g., through the wall of the coronary sinus and into the myocardium below). Then a second anchor structure is percutaneously implanted in the right atrium of the patient outside the ostium of the coronary sinus. Lastly, the distance between the two anchor structures is reduced by percutaneously tightening a linkage (e.g., of suture material) between those structures. Because the coronary sinus is on the heart close to a portion of the annulus of the mitral valve, shortening the distance between the above-mentioned anchor structures shortens the mitral valve annulus. This is beneficial to a patient whose mitral valve annulus is enlarged and whose mitral valve is therefore no longer able to close properly.

Improvements to procedures, prostheses, and related instrumentation of the type illustrated by the foregoing are always sought. For example, it is important to have anchor structures that will not come out of the tissue in which they are implanted.

The percutaneous mitral valve repair procedure mentioned in the preceding paragraphs is only one example of soft body tissue remodeling to which this type of technology may be applied. Other examples include (without limitation) (1) remodeling of a patient's left ventricle, (2) intra-atrial remodeling of a patient's mitral valve annulus, (3) intra-ventricular remodeling of a patient's mitral valve annulus, (4) remodeling of features of a patient's tricuspid valve, and (5) other cardiac applications. What is needed in many soft body tissue remodeling applications is long-term (chronic) durability of the prosthesis under dynamic loading of the prosthesis.

SUMMARY OF THE INVENTION

An illustrative anchor structure for use in soft tissue remodeling includes first and second screw structures that can be driven into tissue a short distance apart along an axis along which the anchor structure will be pulled to remodel the tissue. The screw structures are driven into tissue transverse (e.g., substantially perpendicular) to this axis. A tether or linking member or structure (e.g., of suture material or of suture-like material) extends between head regions of the screw structures (and preferably also beyond the screw structures to the site of another more-distant anchor structure along the above-mentioned axis). A spacer member is located on the linking structure between the head regions of the screw structures. A cinching or clamping member or structure may optionally be disposed on the linking structure where it extends beyond the screw structures to snug the head regions of the screw structures and the spacer member together. Thus we are creating a new type of anchor structure of two screws and a spacer.

The use, in one anchor structure, of two screws that are spaced from one another along the above-mentioned axis (sometimes referred to herein as the tension axis) with a spacer member between head regions of the screws allows one screw to effectively buttress the other screw. This helps to keep the screws transverse to the tension axis, which greatly strengthens the hold of the anchor structure on the tissue.

Other aspects of the invention relate to (1) apparatus and methods for implanting an anchor structure of the general type described above, (2) apparatus and methods for implanting a second anchor structure of the general type described above, and (3) apparatus and methods for maintaining and/or shortening the distance between two anchor structures of the general type described above. Any or all aspects of the invention can be percutaneous, or surgical, or minimally invasive.

The above-mentioned spacer between the screws may be adapted to promote tissue in-growth into and/or around the spacer member.

Although use of pairs of screws (with a spacer between the screws in each pair) is presently preferred, screws of the type shown and described herein may be useful singly as anchor structures. For example, the way in which the linking member is attached to a screw of the type shown herein, and other features of such a screw, may give even a single screw of this type greater tissue holding power than other known single-screw-type anchor structures. Thus one or both of the anchor structures mentioned in the preceding paragraphs may include only a single screw of the type shown herein and still be more effective than a prior, known, single-screw-type anchor structure.

Further features of the invention, its nature and various advantages, will be more apparent from the accompanying drawings and the following detailed description of the preferred embodiments.

BRIEF DESCRIPTION OF THE DRAWINGS

(FIGS. 9 and 10 show all heart structures the same size as FIG. 1. It will be understood, however, that in actual practice the annulus of a patient's mitral valve will typically be larger prior to implanting a prosthesis in accordance with this invention. In other words, in actual practice the mitral valve annulus will be larger in FIGS. 9 and 10 (prior to prosthesis implanting) than in FIG. 1 (after completion of the prosthesis implanting).)

DETAILED DESCRIPTION

The invention will first be illustratively described primarily with reference to an embodiment for performing percutaneous mitral valve repair ("PMVR"). Later in this specification examples of possible alternatives to the first-described embodiment will be described, as will examples of some other possible uses of the invention.

Figure 1:
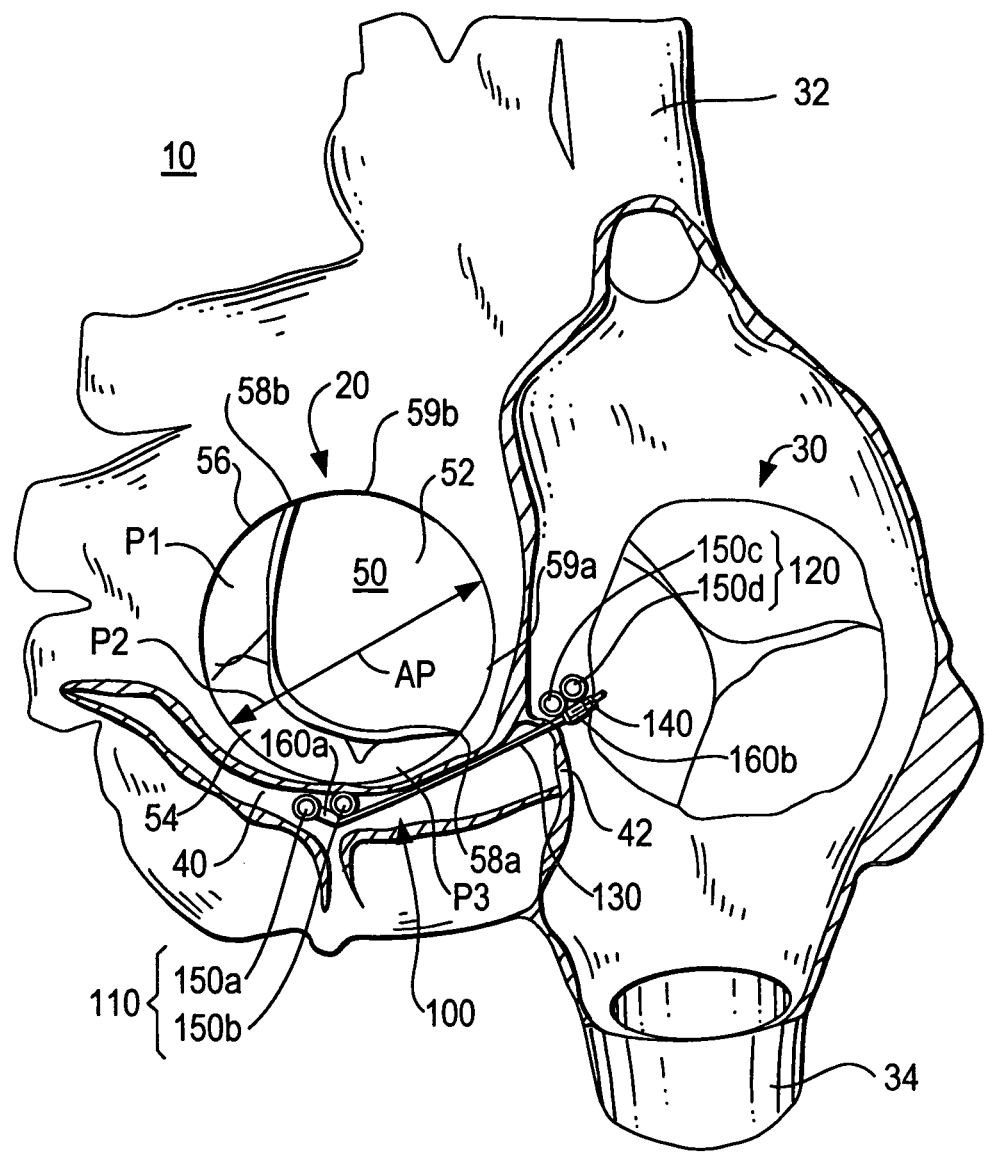
FIG. 1 is a simplified, substantially horizontal (when the patient is standing), cross sectional view of a patient's heart showing illustrative treatment in accordance with the invention. (Another way to describe this cross section is as substantially parallel to the mitral valve annulus.)

The following features of a patient's heart 10 are shown in FIG. 1: left atrium 20, right atrium 30, superior vena cava 32, inferior vena cava 34, coronary sinus 40, ostium 42 of coronary sinus 40 (opening into right atrium 30), and mitral valve 50 (including anterior leaflet 52, posterior leaflet 54 (having three segments P1, P2, and P3), annulus 56, commissures 58a and 58b, and trigones 59a and 59b). The anterior-posterior dimension of mitral valve 50 is labeled AP.

Heart 10 is shown in FIG. 1 with a prosthesis 100 implanted in it in accordance with certain aspects of the invention. Prosthesis 100 includes a first anchor structure 110 that has been implanted in coronary sinus 40 outside posterior mitral valve segment P2. Prosthesis 100 further includes a second anchor structure 120 that has been implanted in right atrium 30 outside the ostium 42 of coronary sinus 40. Prosthesis 100 still further includes a linking member 130 that extends between anchor structures 110 and 120, and that is tensioned to pull those anchor structures toward one another. A clamp 140 on linking member 130 just proximal to anchor structure 140 keeps anchor structures 110 and 120 at the desired spacing from one another along linking member 130.

Looking more closely at FIG. 1, it will be seen that anchor structure 110 includes two screws 150a and 150b (only the head portions of these screws are actually visible in FIG. 1). The distal end of linking member 130 is secured to distal-most screw 150a at or adjacent the head of that screw. Spacer member 160a is disposed around linking member 130 immediately proximal to screw 150a. Linking member 130 passes through an eyelet (not visible in FIG. 1, but shown in later FIGS.) that is mounted on screw 150b adjacent its head. The length of spacer member 160a is approximately equal to the spacing of screws 150a and 150b along linking member 130. Spacer member 160a can be longer or shorter than is shown in FIG. 1 to provide a favorable angle to screws 150a and 150b.

Anchor structure 120 also includes two screws 150c and 150d (again, only the heads being actually visible in FIG. 1). Linking member 130 passes through an eyelet (again, not visible in FIG. 1, but shown in later FIGS.) that is mounted on screw 150c adjacent its head. Proximal to the eyelet on screw 150c, linking member 130 passes through another spacer member 160b, and then through an eyelet on screw 150d (similar to the eyelet on screw 150c). Again, the length of spacer member 160b is approximately equal to the spacing of screws 150c and 150d along linking member 130. As in the case of spacer member 160a, spacer member 160b can be longer or shorter than is shown in FIG. 1 to provide a favorable angle to screws 150c and 150d. Clamp structure 140 is mounted on linking member 130 immediately proximal to the above-mentioned eyelet on proximal-most screw 150d.

Screws 150a and 150b have been driven through the wall of coronary sinus 40 into adjacent heart muscle tissue (preferably in the direction of mitral valve annulus 56, and even more preferably into tissue of that annulus). Screws 150c and 150d are driven into heart muscle tissue of right atrium 30. The above-mentioned Hindrichs et al. reference discusses in detail preferred locations of anchor structures like structures 110 and 120 (although the anchor structures shown herein are new in at least some respects). The Hindrichs et al. reference also discusses tissue structures that anchor structures like 110 and 120 preferably penetrate. All of these principles from the Hindrichs et al. reference are equally applicable to the present invention.

FIG. 1 further shows that the two screws 150a and 150b that form part of anchor structure 110 are preferably spaced from one another approximately along the longitudinal axis of linking member 130. (This axis may sometimes be referred to herein as the tension axis of prosthesis 100.) The same is true for screws 150c and 150d. In addition, all of screws 150 are preferably driven into tissue transverse to the tension axis. For example, driving screws 150 approximately perpendicular to the tension axis is highly desirable but not a requirement for all embodiments of the invention, as long as the screws are transverse to the tension axis to a significant and meaningful degree.

The above-described, pair-wise arrangement of screws 150, together with the provision of a rigid or substantially rigid spacer member 160 between the screws in each pair, provides much stronger and more secure anchoring in tissue than may be achievable, for example, with only a single screw of prior known construction at each of locations 110 and 120. A single screw of prior construction at each location may tend to incline toward the other screw along the tension axis when the linking member is tensioned. In other words, each screw of prior known construction may tend to become aligned with (rather than remaining transverse to) the tension axis. After a single such screw has inclined in this manner, the tensioned linking member 130 is attempting to pull the screw more or less straight out of the tissue that it penetrates. Only a relatively small column of tissue is involved in resisting this attempted pull-out of the screw, and such pull-out of a prior known screw may therefore occur.

With the present invention, however, both screws 150 in each pair of screws tend to remain transverse to the tension axis. For example, the screw 150b or 150c in each pair that is closer to the other pair may act through the associated spacer member 160a or 160b to brace or buttress the other screw 150a or 150d in that pair and thereby help the buttressed screw from becoming aligned with the tension axis. A screw that is driven into tissue and remains transverse to the tension axis provides much stronger holding of the tissue than a screw that can rotate into alignment with the tension axis. An anchor structure (e.g., 110 or 120) including two screws in accordance with this invention is more than twice as strong as a single-screw anchor structure of prior known construction. Moreover, this much stronger anchor structure can be delivered (e.g., percutaneously) through catheter apparatus that is no larger in diameter than would be required for delivery of a single-screw anchor structure of prior known construction.

Later in this specification it will be pointed out that even single-screw anchor structures employing screw structures of the type shown and described herein tend to be stronger than single-screw anchor structures of prior known construction. Thus the screw structures shown and described herein may be usefully and advantageously employed singly in anchor structures that include only one such screw structure.

Figure 2:
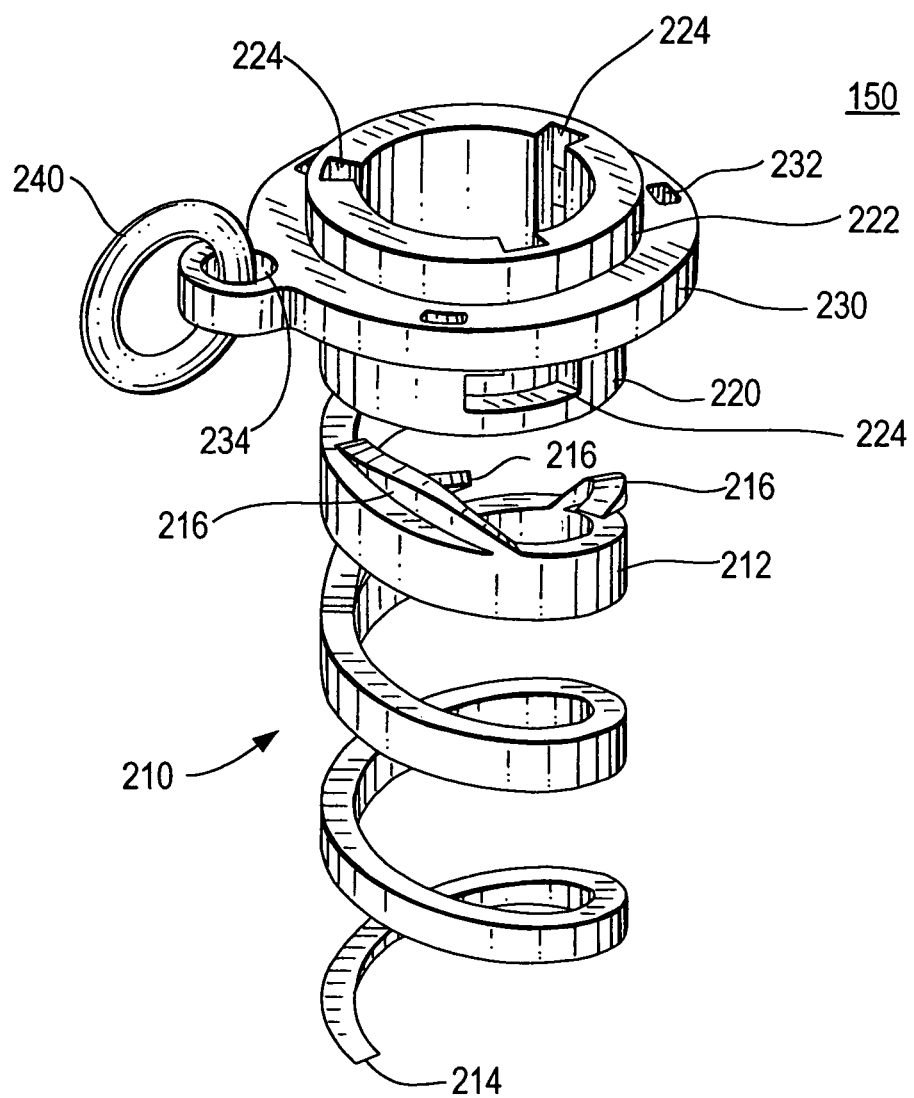
FIG. 2 is a simplified perspective view of an illustrative embodiment of several representative components of an illustrative prosthesis in accordance with the invention.

An illustrative embodiment of a representative screw 150 is shown in more detail in FIG. 2. Screw 150 is actually an assembly of three components: threaded component 210, collar 230, and ring 240. Components 210, 230, and 240 may be made of any suitable bio-compatible material such as 316L stainless steel, L605, Elgiloy, MP35N, gold, platinum, platinum 10 iridium, platinum 20 iridium, titanium, Nitinol, tantalum, niobium, tungsten, Carpenter CCM, a polymer, another material coated with a polymer, etc. One or more of these components may have drug coating(s) and/or be drug eluting. For radiopacity, one or more of the parts may be plated with a high atomic density material such as gold, platinum, tantalum, or the like. One or more of the components may also be clad with one or more layers, such as stainless steel clad with tantalum metal.

Threaded component 210 includes hollow, helical, corkscrew-like, screw portion 212 and hollow head portion 220. Screw portion 212 has a sharply pointed distal tip 214 to facilitate tissue penetration by the screw. Proximal of distal tip 214, screw portion 212 has several helical turns that lead back to head portion 220. These turns may include one or more barbs 216 to resist unthreading of the screw from tissue into which it has been threaded. In particular, each barb 216 is attached to screw portion 212 closer to distal tip 214 and is inclined out and away from the screw portion farther from the distal tip. In other words, each barb 216 is anticlinal from screw portion 212 in the direction opposite the direction in which the screw portion is driven into tissue.

Head portion 220 is basically a hollow cylinder with a flange 222 extending radially outwardly from the proximal end of the cylinder. All portions of screw component 210 other than flange 222 are small enough to pass freely through collar 230. Flange 222 cannot pass through collar 230. Head portion 220 includes features that are usable to releasably hold screw component 210 on screw driving apparatus (not shown in FIG. 2, but detailed later in this specification). These features comprise three approximately T-shaped cut-outs or recesses 224 in head portion 220. These recesses are accessible from the hollow interior of head portion 220, and they are equidistantly spaced around the circumference of the head portion.

Collar 230 fits loosely around the outside of head portion 220, but, as mentioned earlier, flange 222 is too large to pass through the collar. Accordingly, screw component 210 is rotatable about its longitudinal axis relative to collar 230, but when screw 150 is driven into tissue, collar 230 is trapped or captured on the screw by flange 222. Collar 230 includes features that are usable to releasably hold the collar on apparatus that is used to implant screw 150 in a patient. These features are recesses or apertures 232 in or through collar 230. Collar 230 also has a larger aperture 234 for loosely capturing ring 240.

Ring 240 is large enough for linking member 130 to pass freely through the ring. Returning briefly to FIG. 1, ring 240 may be omitted from distal-most screw 150a so that the distal end of linking member 130 can be attached directly to aperture 232 on the collar 230 of that screw. For the other screws (150b-d), however, linking member 130 preferably passes freely through the rings 240 on those screws.

Figure 3:
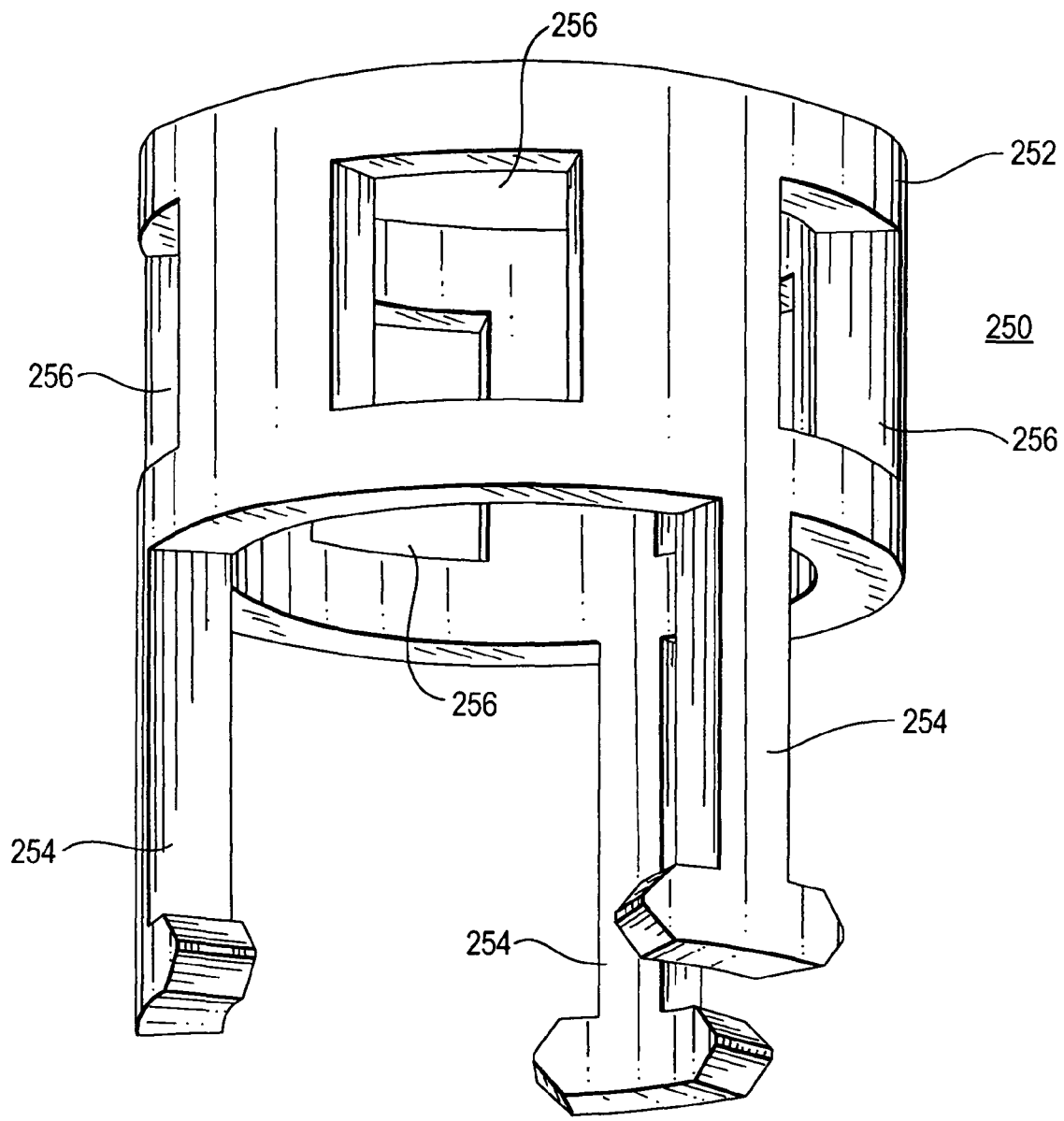
FIG. 3 is a simplified perspective view of an illustrative embodiment of a component of prosthesis delivery and implanting apparatus or instrumentation in accordance with the invention.

FIG. 3 shows a component of apparatus that can be used for releasably holding and driving a screw 150 of the type shown in FIG. 2. This screw holder/driver component 250 includes a hollow-cylindrical proximal portion 252 and three distally extending T-shaped portions 254. Proximal portion 252 includes a plurality of apertures 256 that are usable to help connect screw holder/driver 250 to apparatus components upstream from the holder/driver in a manner that facilitates transmission of torque from those upstream components to holder/driver 250. The component immediately upstream from holder/driver 250 is typically a torqueable flexible shaft (not shown in FIG. 3, but visible in FIG. 14).

T-shaped portions 254 are shaped, sized, and located to fit somewhat loosely into the T-shaped cut-outs or recesses 224 in the head portion 220 of a screw 150. Although not shown in this condition in FIG. 3, T-shaped portions 254 are resiliently biased to deflect radially inwardly toward one another. When thus deflected radially inwardly, the enlarged, distal, free end parts of T-shaped portions 254 can pass freely into or out of the hollow cylindrical head 220 of a screw 150. However, T-shaped portions 254 can be deflected radially outwardly to the positions shown in FIG. 3 by inserting a properly sized cylindrical member (not shown in FIG. 3) into the interior of component 250. In this condition, T-shaped portions 254 fit into T-shaped cut-outs or recesses 224 in the head portion of a screw 150. This both holds the screw to component 250 and allows the screw to be driven by rotating component 250. When the screw has been driven into tissue to the desired degree, the above-mentioned cylindrical member can be withdrawn from the interior of holder/driven 250. This allows the enlarged distal ends of T-shaped fingers 254 to deflect inwardly and thereby exit from the corresponding portions of T-shaped recesses 224 in the screw. The screw is therefore no longer held on the apparatus by inter-engagement of elements 224 and 254.

The particular structure shown and described above for releasably holding screw 150 on holder/driver 250 (e.g., the use of T-shaped portions 254 that are resiliently biased to deflect inwardly) is only one example of many possible ways that this function can be achieved. For example, features like 224 and 254 could have many other complementary shapes that would serve the purposes of releasably holding components 150 and 250 together and permitting the transmission of torque from component 250 to component 150 while those components are held together. The cylindrical member mentioned in the preceding paragraph may be used as a depth gauge for the driving of the associated screw. For example, when the distal end of this cylindrical member reaches the surface of the tissue, it is thereby known that the associated screw has been driven far enough into the tissue. Indeed, the structure may be arranged so that the tissue pushes the cylindrical member out of the screw, thereby decoupling the screw from its holder 250 and automatically stopping further driving of the screw at the proper depth of tissue penetration.

Figure 4:
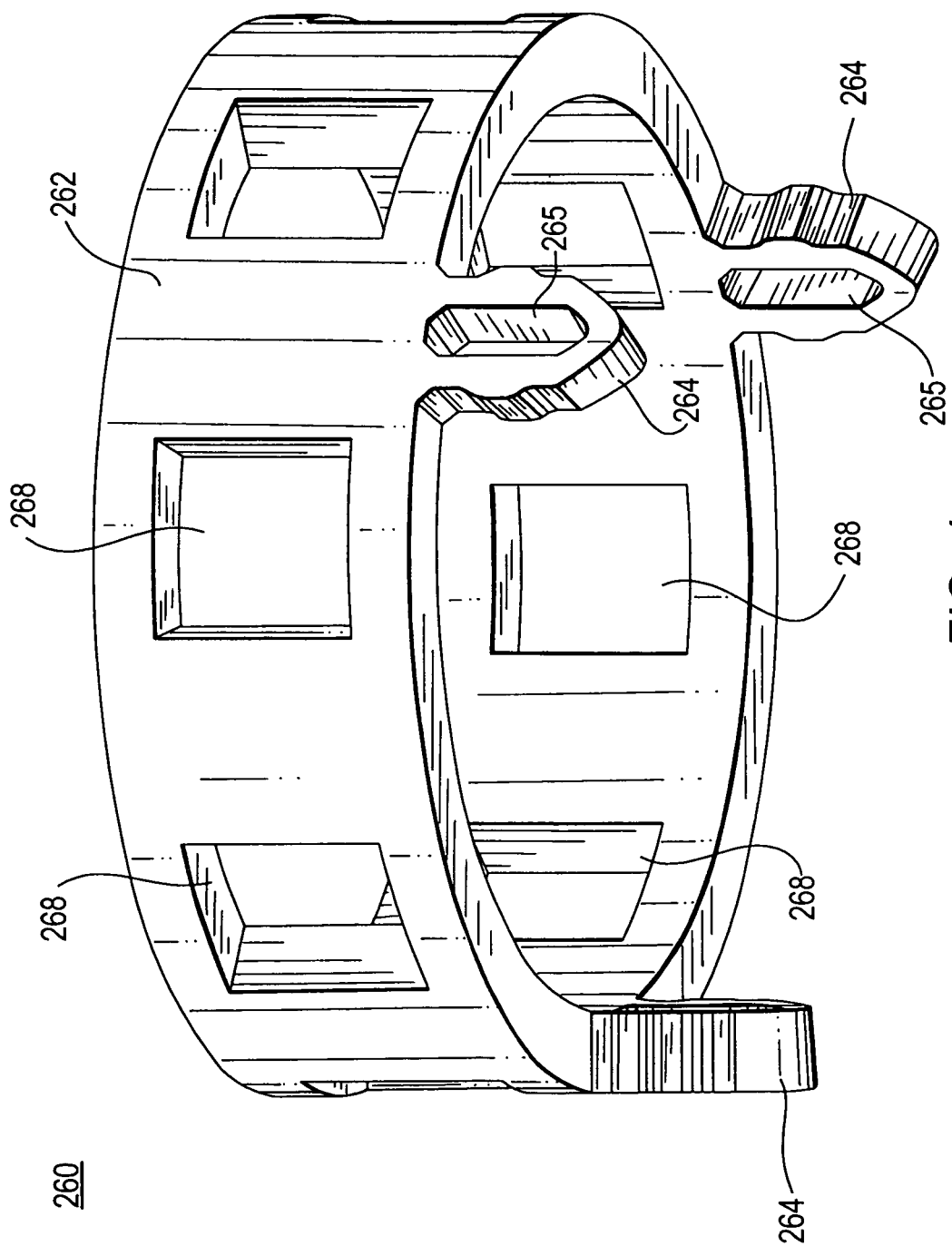
FIG. 4 is a simplified perspective view of an illustrative embodiment of another component of prosthesis delivery and implanting apparatus in accordance with the invention.

FIG. 4 shows a component of apparatus that can be used to releasably hold a screw collar 230 of the type shown in FIG. 2. This collar holder 260 includes a hollow cylindrical proximal portion 262 and three distally extending gripper fingers 264. Proximal portion 262 can fit concentrically but loosely around the outside of holder/driver 250 (FIG. 3). Proximal portion 262 includes a plurality of apertures 266 that are usable to help connect collar holder 260 to upstream apparatus components. Fingers 264 fit into apertures 232 in collar 230. In the radial direction this fit is preferably loose. In the circumferential direction, however, this is a force fit, involving some resilient compression of the apertures 265 through fingers 264. A collar 230 can therefore be pressed onto holder 260, and it will thereafter remain on the holder. However, the collar can be pushed off the holder when the proximal surface of the threaded portion 210 associated with that collar is pushed distally with sufficient force. Alternatively, a separate catheter-like pusher could be used to push collar 230 off holder 260.

Figure 5:
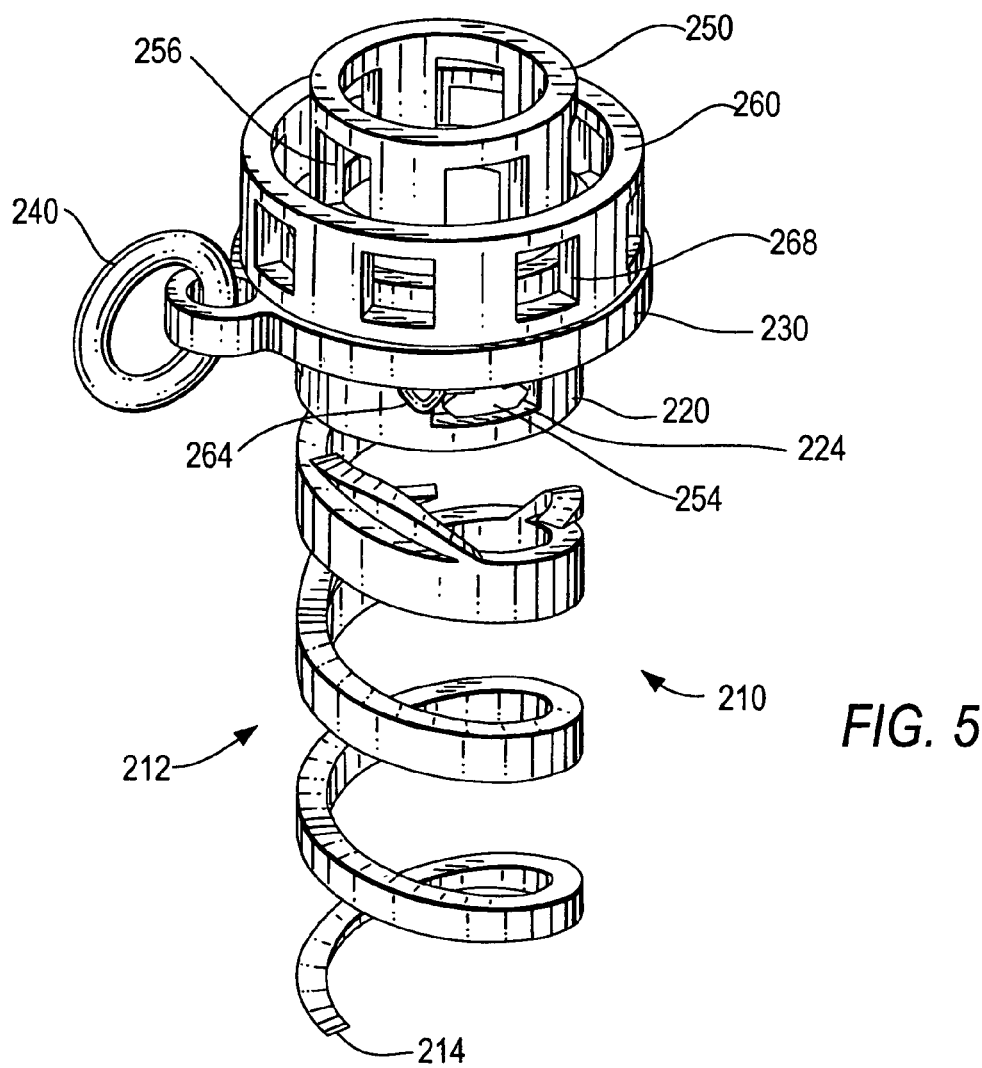
FIG. 5 is generally similar to FIG. 2, but with the components shown in FIGS. 3 and 4 added.

FIG. 5 shows an assembly of the elements that are shown individually in FIGS. 2-4. Screw component 210 is releasably retained on holder/driver component 250 by the presence of T-shaped portions 254 of component 250 in complementary recesses 224 in the head portion 220 of screw portion 210. The presence of T-shaped portions 254 in recesses 224 also makes it possible to rotate screw component 210 about its longitudinal axis by rotating holder/driver component 250 about that axis. Collar 230 is releasably retained on collar holder 260 by the force-fitted presence of fingers 264 from holder 260 in collar apertures 232. Components 210 and 250 are rotatable relative to components 230 and 260 about the longitudinal axis of component 210. FIG. 5 omits the apparatus component that is required to keep T-shaped portions 254 deflected radially outward and therefore in recesses 224 as shown in FIG. 5. Note that the free ends of fingers 264 preferably extend completely through and beyond the lower surface of collar 230. This permits the free ends of fingers 264 to engage or penetrate the surface of the tissue into which threaded portion 210 is going to be driven. Such engagement or penetration helps to stabilize the assembly at a desired location on the surface of the tissue during driving of threaded portion 210, and also prevents collar 230 from undesirably rotating with threaded portion 210 as the threaded portion is rotated to drive it into the tissue.

Again, the particular structures shown in the FIGS. described thus far for releasably holding collar 230 on holder 260 are only illustrative, and any of many other structures can be used for this purpose instead if desired. For example, more positive threaded or bayonet-type structures can be used instead of the above-mentioned force-fit connection.

Figure 6:
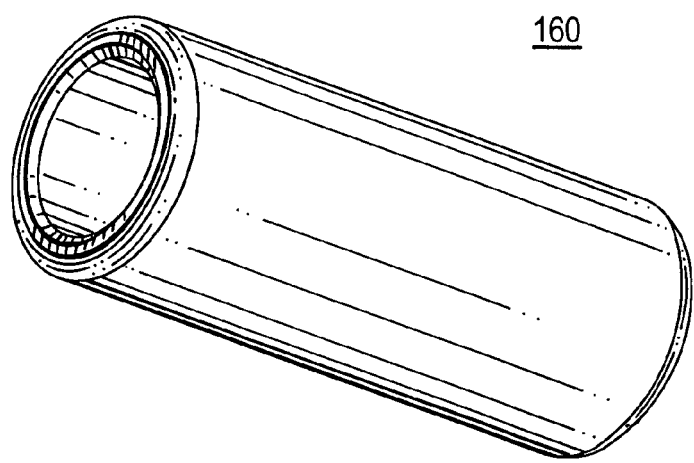
FIG. 6 is a simplified perspective view of an illustrative embodiment of another representative component of an illustrative prosthesis in accordance with the invention.

Further components of the illustrative prosthesis being described are spacer members 160a and 160b. FIG. 6 shows an illustrative embodiment of a typical spacer member 160 in more detail. As shown in this FIG., a spacer member 160 can be a hollow cylinder (e.g., of a bio-compatible metal). The hollow center of spacer member 160 is preferably large enough to allow the spacer member to slide freely along the length of linking member 130. However, the diameter of spacer member 160 should be large enough so that the ends of the spacer member can engage the head portions of screws 150 that the spacer member abuts.

Spacer member 160 may have features beyond those shown in FIG. 6. For example, spacer member 160 may have perforations, a dacron cover, and/or other features to promote tissue in-growth and anchoring in the patient. Suitable materials for spacer member 160 include those mentioned above for components 210, 230, and 240.

Figure 7:
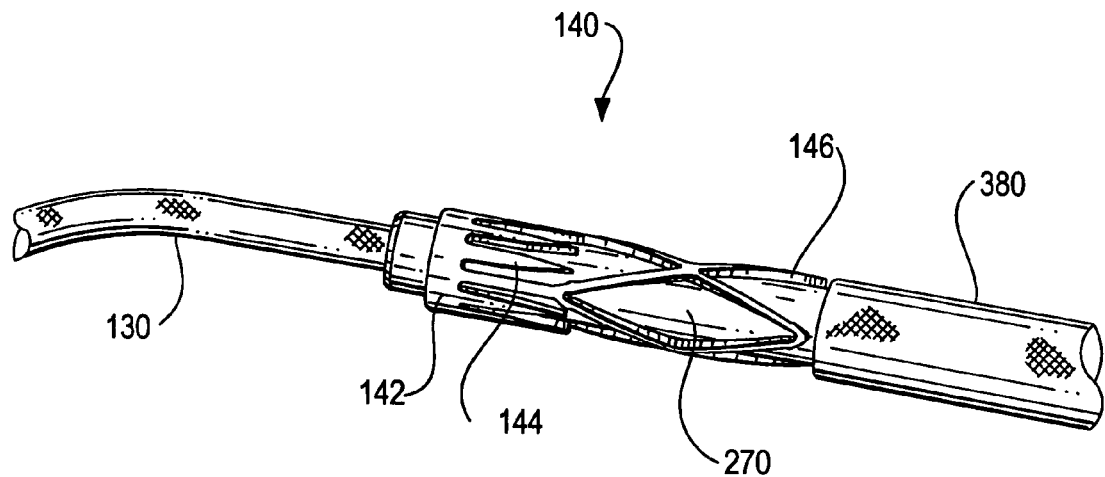
FIG. 7 is a simplified elevational view of an illustrative embodiment of representative components of an illustrative prosthesis, with illustrative apparatus for delivering and implanting one of those components, all in accordance with the invention.
Figure 8:
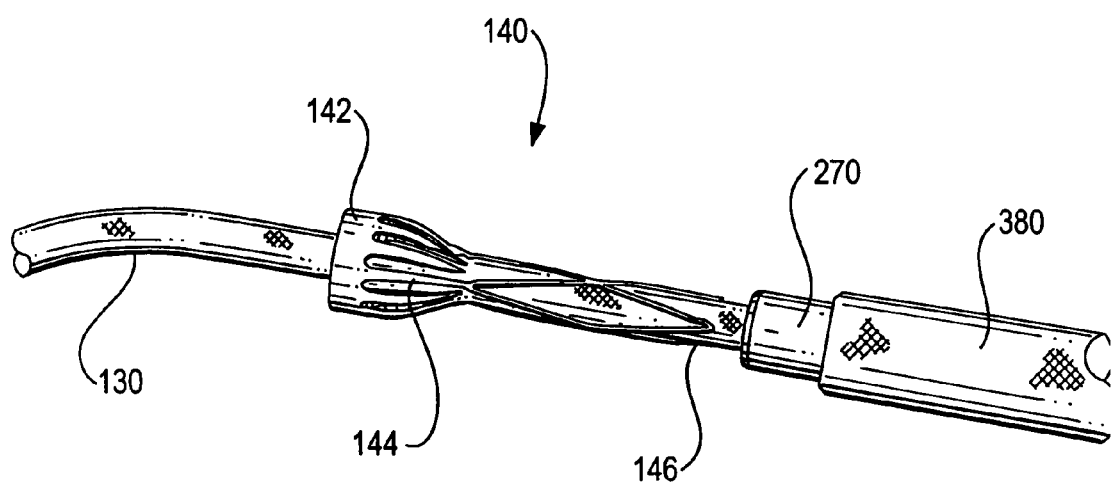
FIG. 8 is similar to FIG. 7, but shows a subsequent stage in use of what is shown in FIG. 7 in accordance with the invention.

Still another component of the apparatus is clamp structure 140. An illustrative embodiment of clamp structure 140 is shown in FIGS. 7 and 8, with some other apparatus also visible. In FIG. 7 clamp structure is disposed concentrically around a hollow tube 270 through which linking member 130 passes loosely. In FIG. 8 tube 270 has been removed to release clamping structure 140 to engage linking member 130. Note that the distal direction is to the left in FIGS. 7 and 8. This is consistent with FIG. 1.

Clamp structure 140 (e.g., of bio-compatible metal) is resiliently biased to assume the shape shown in FIG. 8, but it can be elastically deflected to the shape shown in FIG. 7. (Alternatively clamping structure 140 could be plastically deformed from the shape shown in FIG. 7 to the shape shown in FIG. 8.) Proceeding from left to right in FIG. 7, clamp structure 140 includes (1) a hollow cylindrical portion 142, (2) a plurality of relatively short fingers 144 that extend in the proximal direction from cylindrical portion 142 and that are resiliently biased to deflect inwardly, and a (3) plurality of relatively long fingers 146 that also extend in the proximal direction from cylindrical portion 142 and that are intercalated with fingers 144. Proximal free end portions of fingers 146 are also resiliently biased to deflect inwardly. The inward bias of fingers 144 and 146 helps to hold clamp structure 140 on tube 270, albeit in such a way that tube 270 can be withdrawn from structure 140 when desired.

The proximally directed free ends of fingers 144 are preferably sharp enough to dig into linking member 130 when tube 270 is withdrawn from inside structure 140 (see FIG. 8). This prevents clamp structure 140 from moving proximally along linking member 130 once structure 140 has thus engaged member 130. This resistance to movement of structure 140 may be facilitated or enhanced by making linking member 130 of braided suture material as shown in FIGS. 7 and 8, but other constructions of linking member 130 are also possible, as will be further discussed later in this specification.

The proximally directed free ends of fingers 146 are less sharp and are intended to press inwardly on linking member 130 for such purposes as to stabilize clamp structure 140 on linking member and to prevent a braided linking member 130 from unraveling when it is subsequently cut proximal to clamp structure 140.

Having described an illustrative embodiment of a prosthesis 100 in accordance with the invention, we turn now to a description of illustrative methods and apparatus for implanting such a prosthesis, also in accordance with the invention. The illustrative methods and apparatus that will first be described are percutaneous.

Figure 9:
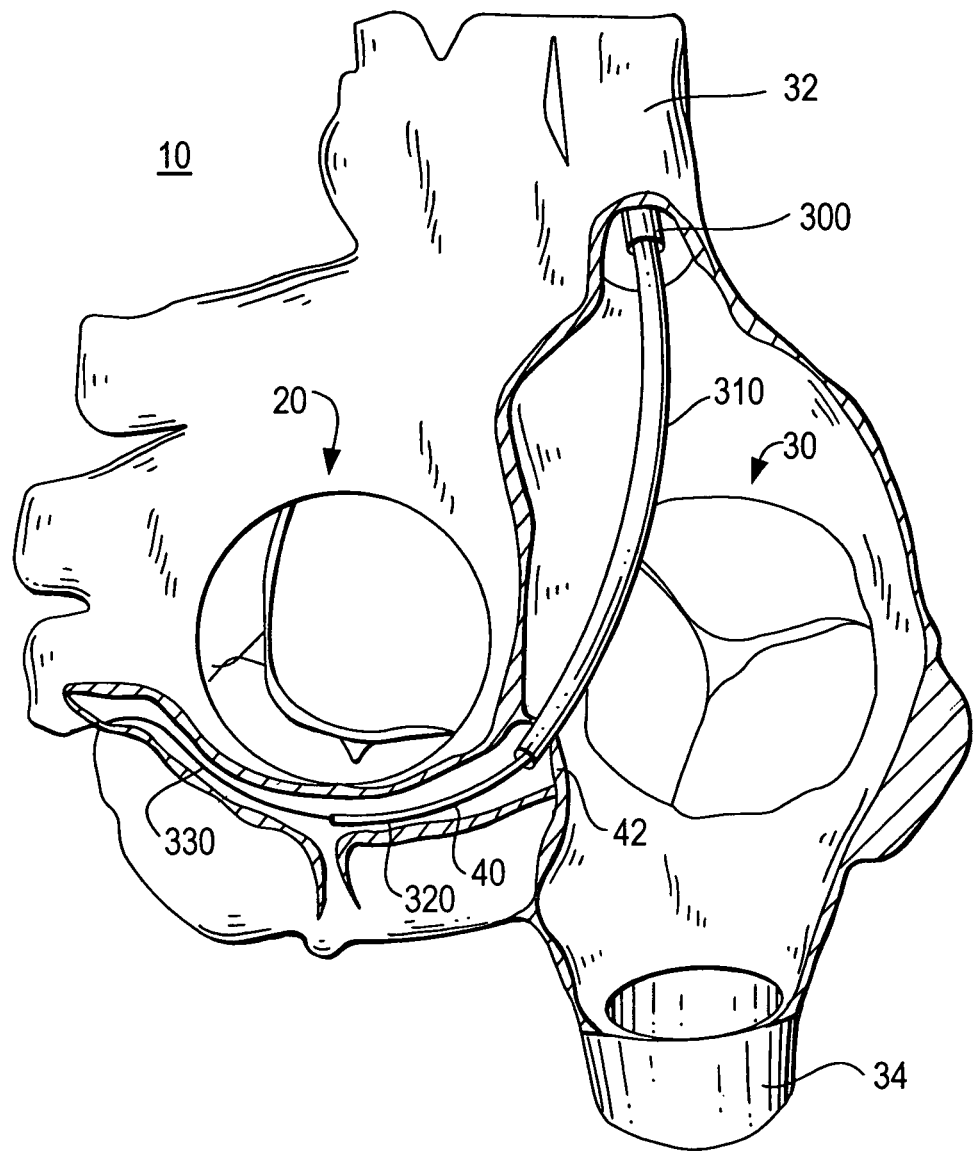
FIG. 9 is similar to FIG. 1, but shows an illustrative embodiment of some of the instrumentation that can be used in the implanting of a prosthesis in accordance with the invention.

An illustrative method begins with inserting an introducer tube 300 into the superior vena cava 32 of the patient as shown in FIG. 9. This may be done by starting from an introduction point into the patient along the patient's jugular vein. A possible alternative approach is via inferior vena cava 34. Either of these approaches gives access to right atrium 30. Although the distal end of introducer 300 is shown relatively low in FIG. 9, it may actually be higher and therefore out of sight in what is shown in that FIG.

The next step in the illustrative method being discussed is to insert a guide catheter or sheath 310 into the patient via introducer 300 and to extend that guide catheter into the ostium 42 of coronary sinus 40 as is also shown in FIG. 9.

The next step is to extend an obturator or dilator 320 and a wire 330 into guide catheter 310 and then from the distal end of the guide catheter farther into coronary sinus 40 (continue to see FIG. 9). Obturator 320 provides support for wire 330 to help the distal-most portion of the wire extend into coronary sinus 40, and possibly into a tributary thereof, well beyond the point at which the distal anchor structure 110 of prosthesis 100 will be implanted.

The next step (illustrated by FIG. 10) is to advance guide catheter 310 to the desired location of distal anchor structure 110. Obturator 320 is removed at this time.

Figure 10:
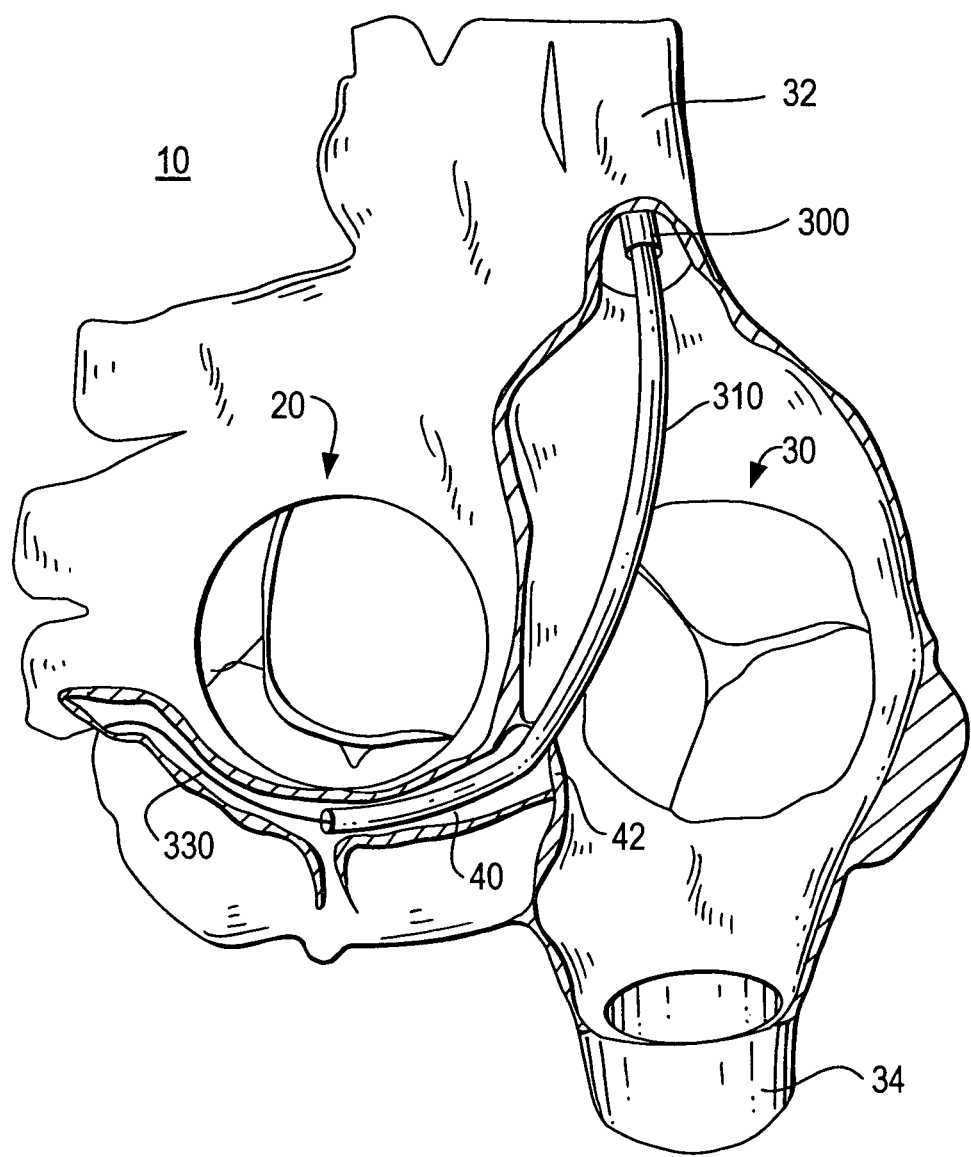
FIG. 10 is similar to FIG. 9, but shows a later stage in use of what is shown in FIG. 9 in accordance with the invention.
Figure 11:
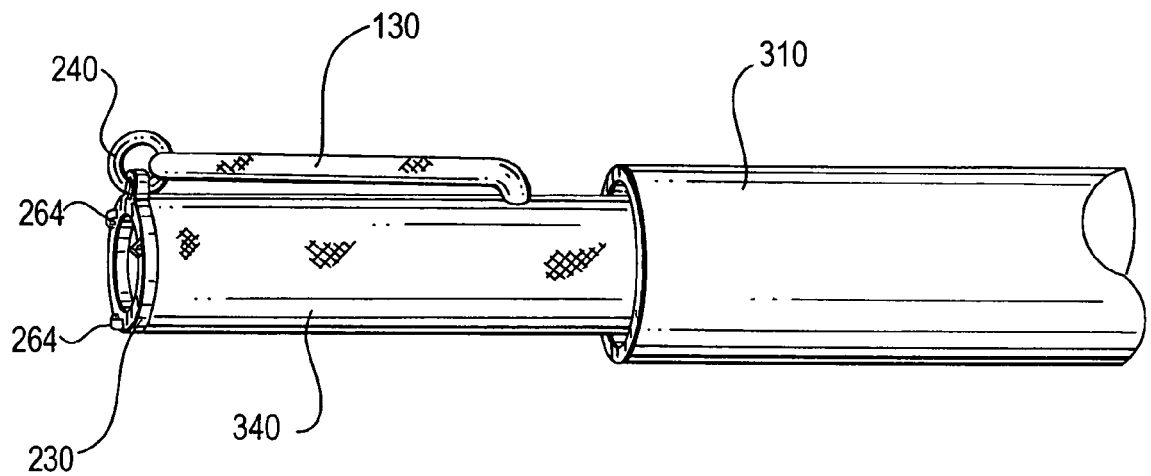
FIG. 11 is a simplified elevational view of an illustrative embodiment of representative components of an illustrative prosthesis, with illustrative apparatus for delivering and implanting those components, all in accordance with the invention.
Figure 33:
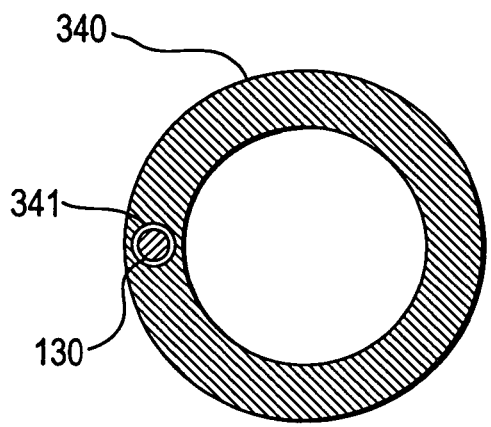
FIG. 33 is a simplified cross section of an illustrative embodiment of certain components in accordance with the invention.

The next step is to introduce into guide catheter 310 and "over" wire 330 a delivery system for the first part of distal anchor structure 110. In particular, this is a delivery system for implanting screw 150a. FIG. 11 shows a first part of this delivery system extending from the distal end of guide catheter 310. For clarity, no tissue is shown in FIG. 11. This FIG. also omits wire 330, although it will be understood that in actual use wire 330 may be present. The portion of the delivery system shown in FIG. 11 includes tubular member 340 extending from the distal end of guide catheter 310. A collar holder 260 (not visible in FIG. 11) is secured inside the distal end of tubular member 340, and a collar 230 is removably mounted on the distally extending gripper fingers 264 of that collar holder in the manner described earlier in this specification. The distal end of linking member 130 (which extends from a side lumen 341 of tubular member 340 (see FIG. 33)) is secured to ring 240 on collar 230. Alternatively, ring 240 could be omitted, and the distal end of linking member 130 could be secured directly to the aperture 234 in collar 230 that ring 240 is shown passing through. A proximal portion of linking structure 130 preferably passes along the side lumen 341 of tubular member 340 upstream from what is shown in FIG. 11 to help ensure that linking member 130 does not become undesirably wrapped around other components of the apparatus (see again FIG. 33). Wire 330 (not shown in FIG. 11) can extend from the distal end of the assembly of elements 340/260/230 to its distal end to the left of what is shown in FIG. 11. Wire 330 can be withdrawn once the elements shown in FIG. 11 have reached the desired location along coronary sinus 40 (or the wire could be withdrawn earlier, e.g., after the distal end of guide catheter 310 has reached its desired location along coronary sinus 40 as shown in FIG. 10).

Figure 12:
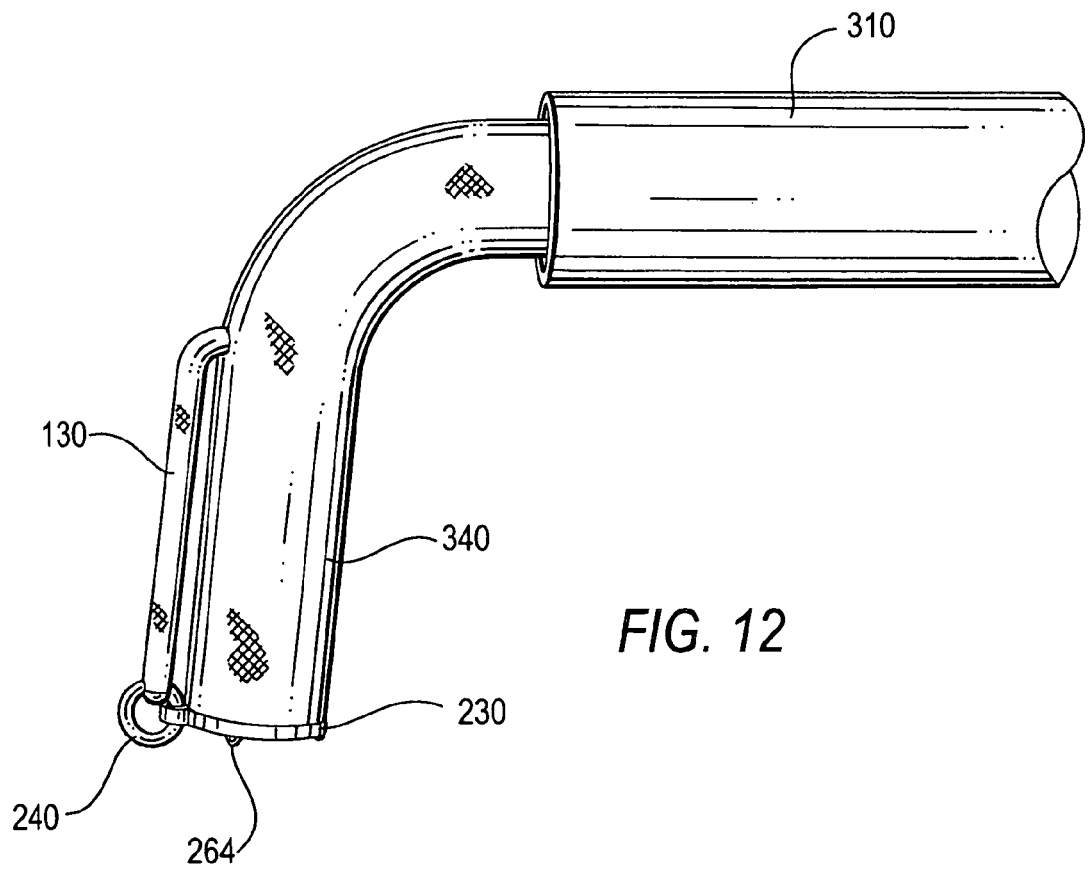
FIG. 12 is similar to FIG. 11, but shows a subsequent stage in use of what is shown in FIG. 11.
Figure 13:
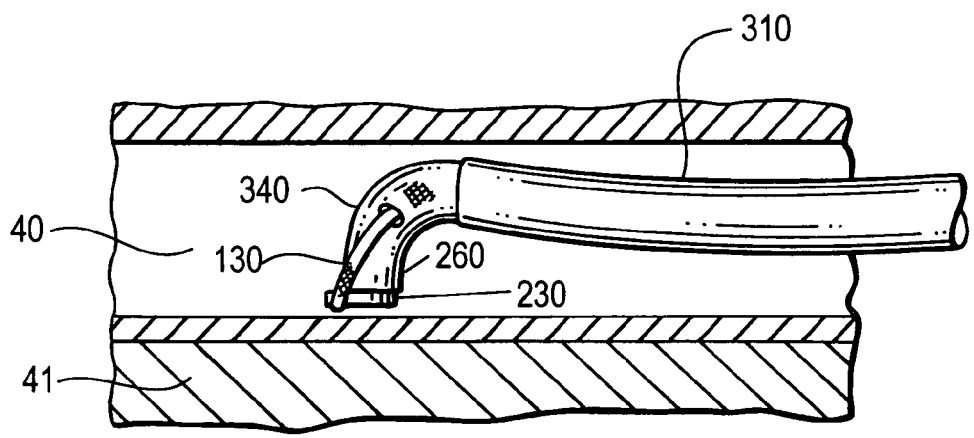
FIG. 13 is a simplified sectional view of a portion of what is shown in FIGS. 1, 9, and 10 at a particular, relatively early stage in implanting a prosthesis in accordance with the invention.

The distal portion of tubular member 340 is "steerable" (see FIG. 12). This means that the distal portion of tubular member 340 can be controllably deflected transverse to the longitudinal axis of guide catheter 310 (or to the longitudinal axis of the proximally adjacent portion of tubular member 340). The amount of this deflection is preferably up to about 90° or more. In other words, the distal portion of tubular member 340 can be deflected so that it becomes substantially perpendicular to the proximally adjacent portion of that member. This allows the distal portion of tubular member 340 to be aimed at the side wall of coronary sinus 40 as shown in FIG. 13. Indeed, it may be desirable to aim the distal end of tubular member 340 (and therefore collar 230) at a particular portion of the circumference of coronary sinus 40 in order to get good anchoring of the anchor structure to be implanted in the strongest possible tissue of the heart (see the above-mentioned Hindrichs et al. reference, which discusses optimal placement of anchor structures in the coronary sinus and elsewhere in the heart). The steerability of tubular member 340 may be unidirectional, bidirectional, or multidirectional (in other words, in one direction transverse to the longitudinal axis of the remainder of the structure, in either of two directions transverse to that longitudinal axis, or in any one of several directions transverse to that longitudinal axis).

Although not shown in FIG. 13, the relative sizes and shapes of the tissue and apparatus components may be such that transverse deflection of the distal portion of the structure causes a substantial distortion of coronary sinus 40 at that location. In particular, the "back" side of the apparatus (i.e., adjacent the bend in tubular member 340) may deflect the adjacent portion of coronary sinus 40 outwardly. This helps to push collar 230 firmly against the opposite side of the coronary sinus, which facilitates driving the threaded portion 210 of a screw into the tissue as described below. (The same kind of distortion of coronary sinus 40 may occur in connection with FIG. 19, although this distortion is again not actually shown in that FIG.)

Figure 14:
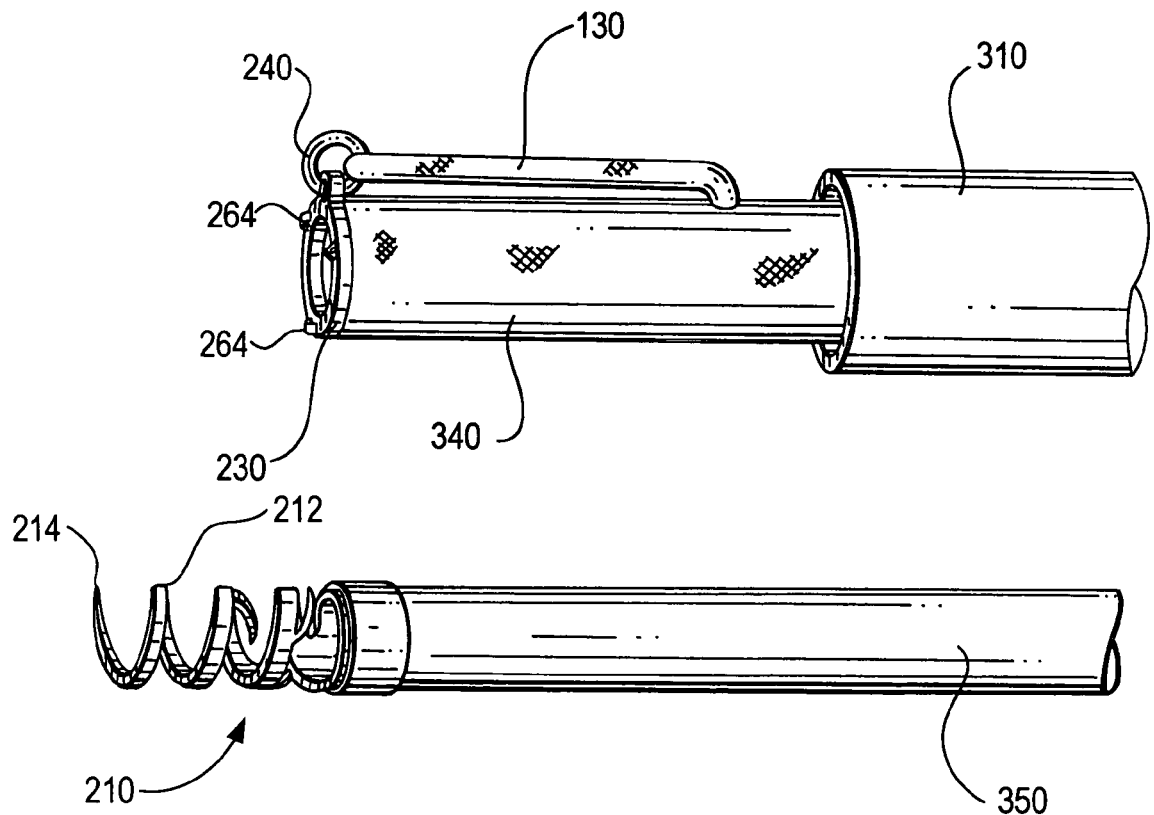
FIG. 14 is a simplified perspective view of an illustrative embodiment of representative components of an illustrative prosthesis, with illustrative apparatus for delivering and implanting those components, all in accordance with the invention.

Further components of the delivery system for implanting screw 150a are shown in FIG. 14. These components include tubular member 350 with a screw holder/driver attached to its distal end and threaded component 210 held on that holder/driver. Another tube or plug (not visible) is disposed coaxially inside elements 350 and 250 to initially keep T-shaped portions 254 of holder/driver 250 deflected radially outward in the complementary recesses 224 in threaded component 210 and thereby hold threaded component 210 on holder/driver 250.

Figure 15:
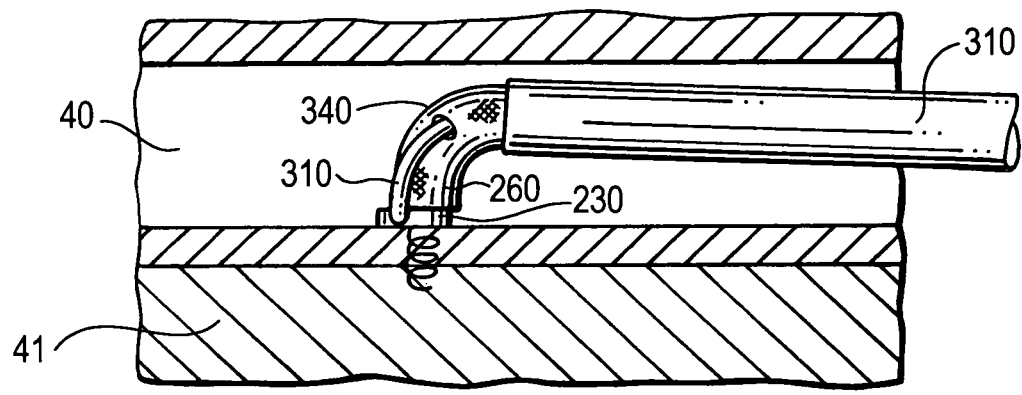
FIGS. 15-17 are similar to FIG. 13 for successive subsequent stages in implanting a prosthesis in accordance with the invention.

Components 350/250/210 are insertable coaxially into and along tubular member 340 from the proximal end of member 340. Components 350/250/210 may be inside member 340 when member 340 is inserted into guide catheter 310. When the distal portion of member 340 is properly aimed toward the side wall of coronary sinus 40 as shown in FIG. 13, tubular member 350 may be pushed distally and rotated about its longitudinal axis to cause threaded portion 210 to begin to emerge from the distal end of assembly 340/260/230 and to begin to threadedly penetrate the side wall of coronary sinus 40 and adjacent heart tissue 41 (see FIG. 15). Note again that components 310 and/or 340 preferably bear on the wall of coronary sinus 40 approximately opposite the tissue-entry point of threaded portion 210 to help force threaded portion 210 into the tissue. Component 350 is preferably sufficiently laterally flexile to follow the lateral (steering) deflection of component 340. Component 350 is also able to transmit to component 210 the torque necessary to thread component 210 into tissue.

When threaded portion 210 has been driven sufficiently far into tissue 40/41 so that flange 222 (e.g., FIG. 2) contacts collar 230 and the collar is at least in contact with tissue 40/41, driving of threaded portion 210 is stopped. The next step is to retract the above-mentioned tube or plug from inside screw holder/driver 250. This allows T-shaped portions 254 of holder/driver 250 to deflect radially inwardly, which releases threaded portion 210 from holder/driver 250. To also release collar 230 from collar holder 260, tubular member 350 is pushed distally while tubular member 340 is pulled proximally. Alternatively, only one of members 340 and 350 may be pushed or pulled while the other member is held relatively stationary. These actions force collar 230 off the gripper fingers 264 of collar holder 260. Screw 150a is now implanted in tissue 40/41 and fully released from delivery apparatus 340/260/350/250, although the screw is still attached to the distal end of linking member 130.

Figure 16:
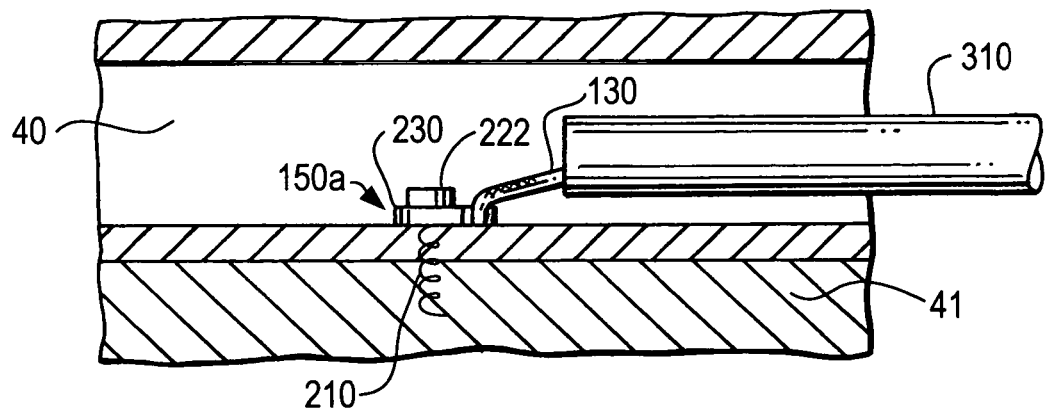

The next step is to re-straighten the steerable distal portion of tubular member 340 and withdraw components 340, 360, 350, and 250 from the patient. The condition of the apparatus is now as shown in FIG. 16.

Figure 17:
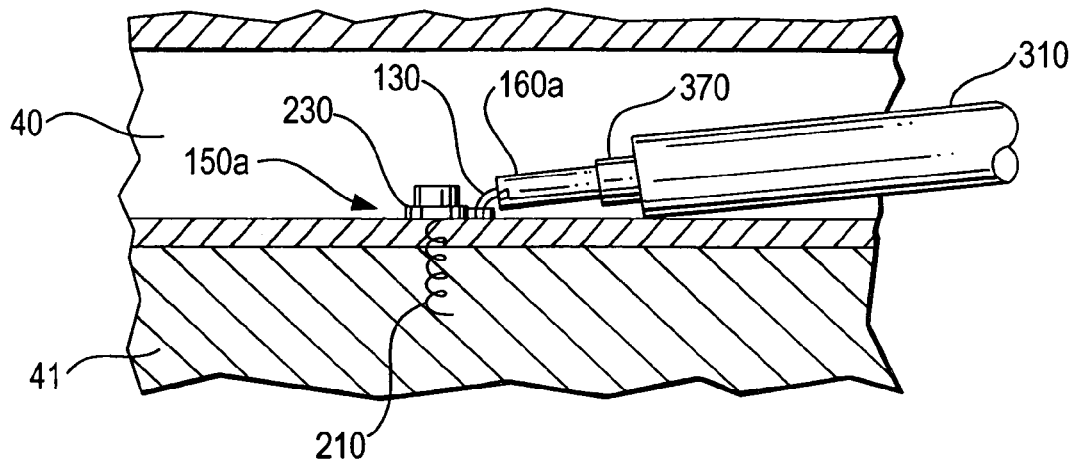

The next step is to push spacer member 160a into the patient over linking member 130. A proximal portion of linking member 130 may transition from a suture-like material to a wire to facilitate getting spacer member 160a (and other apparatus) into the patient over linking member 130. A tubular pusher 370 may be placed over linking member 130 proximal to spacer member 160a for use in pushing spacer member 160a into the patient and into abutment with screw 150a as shown in FIG. 17.

After spacer member 160a is in place, tubular pusher 370 may be withdrawn from the patient.

Figure 18:
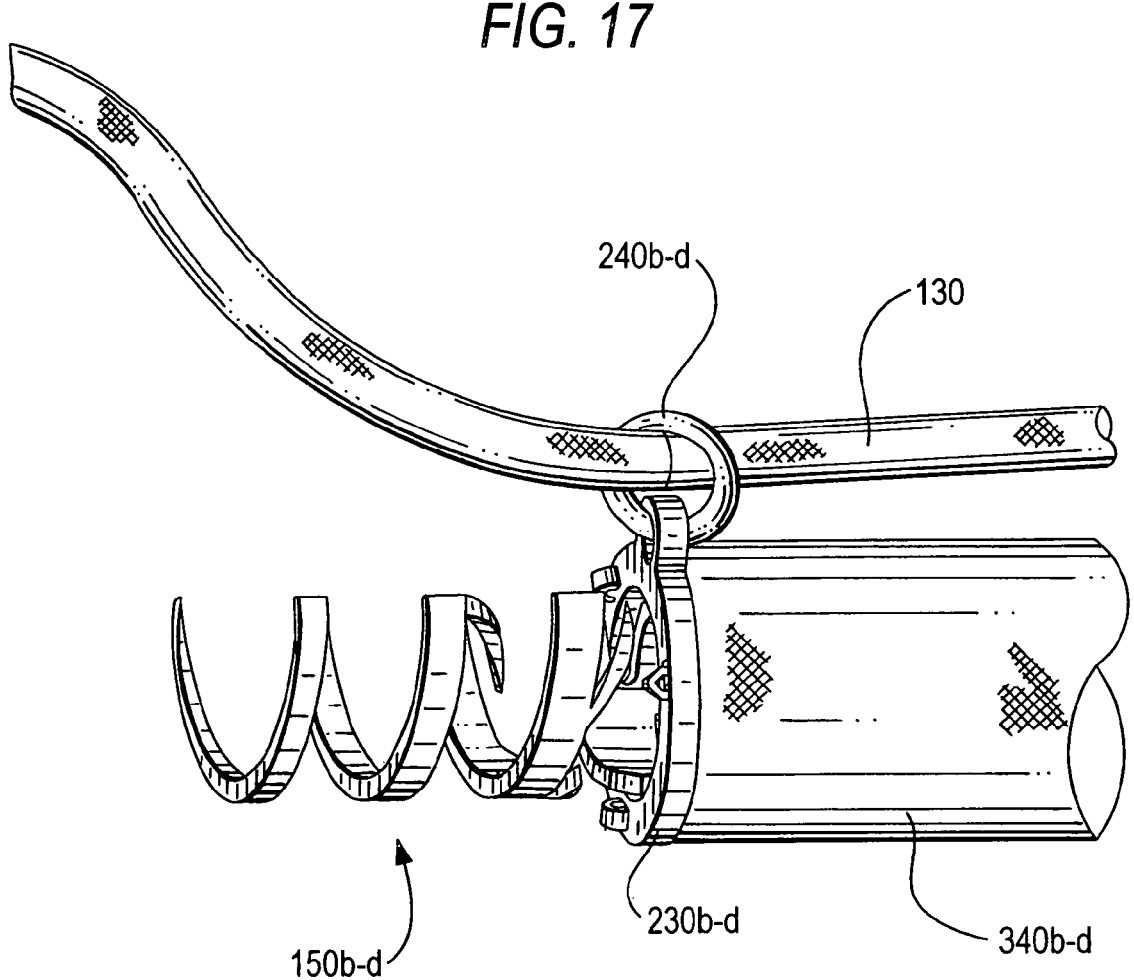
FIG. 18 is generally similar to FIG. 14, but with certain components additionally assembled in accordance with the invention.

The next step is to position the distal end of guide catheter 310 appropriately for implanting second screw 150b. Apparatus for delivering second screw 150b can then be inserted into the patient via guide catheter 310. The delivery system for second screw 150b can be very similar to the above-described delivery system for first screw 150a. The only significant difference is that in the case of second screw 150b linking member 130 passes loosely through the ring 240 of the second screw rather than being secured to the screw as in the case of first screw 150a. FIG. 18 illustrates this type of loose passage of linking member 130 through a ring 240 on a screw 150 like screw 150b.

Because the delivery system for screw 150b can be so similar to the delivery system for screw 150a, the same reference numbers will be used again (but with a "b" suffix) for components of the second screw delivery system. Discussion of delivery and implanting of the second screw can also be somewhat abbreviated because it is so similar to the above-described delivery and implanting of the first screw.

Figure 19:
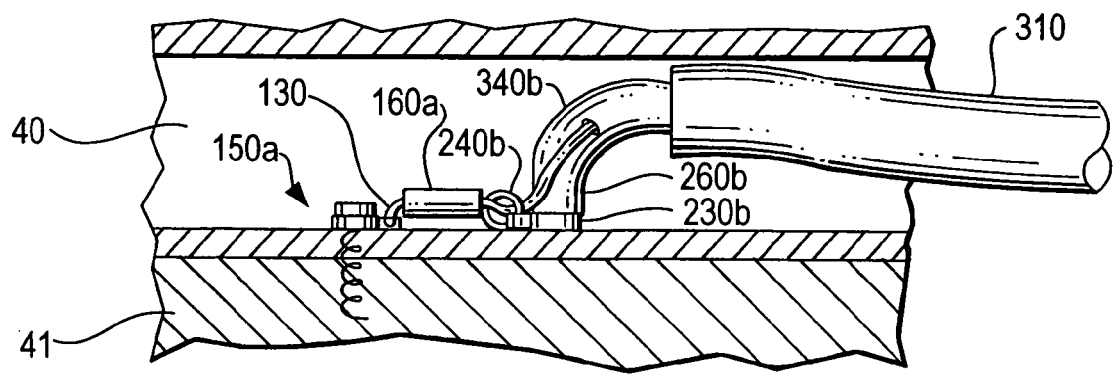
FIGS. 19-23 are again similar to FIGS. 13 and 15-17, but show successive, more subsequent stages in implanting a prosthesis in accordance with the invention.

FIG. 19 shows the condition of the apparatus after components 340b, 260b, and 230b for second screw 150b have been extended from the distal end of guide catheter 310 and steered (i.e., laterally deflected) toward the desired point on the side wall of coronary sinus 40. Note the passage of linking member 130 through ring 240b on the collar 230b that will form part of second screw 150b. Passage of linking member 130 through ring 240b is facilitated by the above-mentioned proximal wire end portion of linking member 130, which remains outside the patients body and is available for use in helping to place successive components and instrumentalities on linking member 130.

Figure 20:
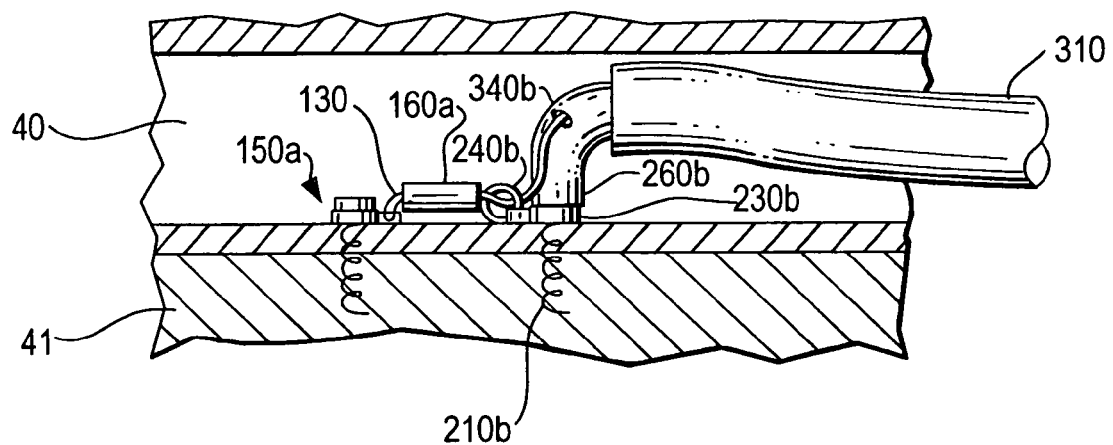

After the condition shown in FIG. 19 is attained, the threaded portion 210b of second screw 150b can be advanced distally through assembly 340b/260b/230b and driven into tissue 40/41 as described above for the corresponding components associated with screw 150a (see FIG. 20).

Figure 21:
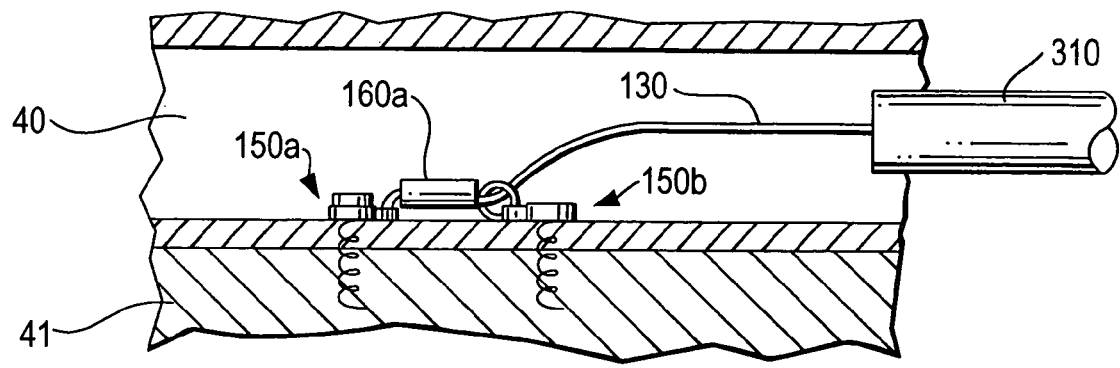

After threaded portion 210b has been driven into tissue 40/41, threaded portion 210b can be released from its holder/driver (not visible, but inside tubular member 340b) as described earlier for the corresponding parts associated with screw 150a. Then collar 230b can be released from its holder 260b in the same manner as described above for the corresponding parts associated with screw 150a. The distal end of tubular member 340b can be re-straightened, and all of the delivery apparatus for screw 150b can be proximally withdrawn from the patient via guide catheter 310. The condition of the apparatus is now as shown in FIG. 21.

Figure 22:
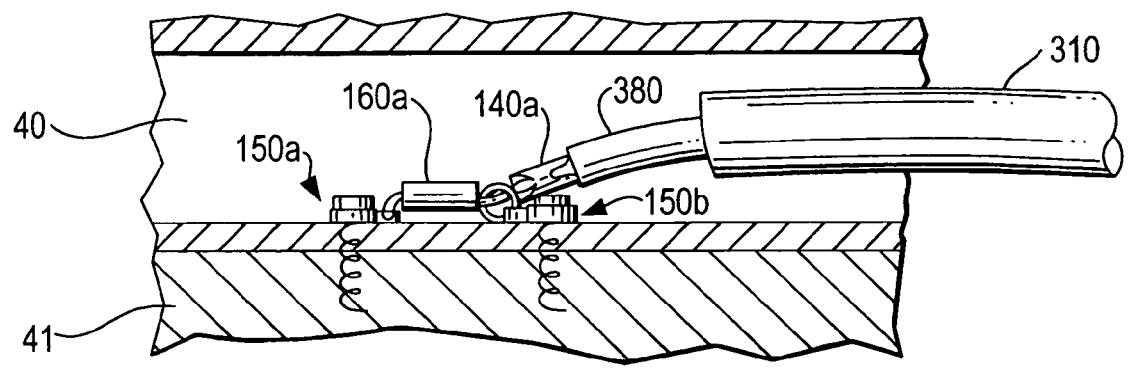
Figure 23:
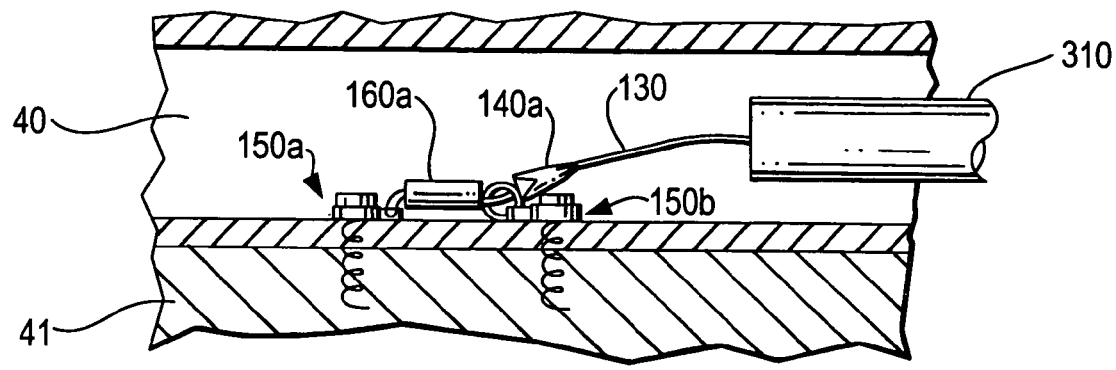

Although perhaps not necessary, a clamp structure 140a can now be put on linking member 130 immediately proximal to screw 150b. This optional process is shown in FIGS. 22 and 23. In FIG. 22 clamp structure 140a and associated delivery apparatus (e.g., as shown in more detail in FIG. 7) is loaded onto linking member 130 and introduced into the patient via guide catheter 310. The delivery apparatus for clamp 140a includes a tube 270 inside the clamp (see FIG. 7) and another tubular member 380 disposed concentrically around the outside of tube 270 and bearing (at its distal end) on the proximal end of the clamp. FIG. 22 shows clamp 140a pushed up against structure of screw 150b and therefore ready for release onto linking member 130.

Clamp 140a is released onto linking member 130 by pulling back on tube 270 while holding tubular member 380 stationary (see also FIG. 8). Proximal withdrawal of tube 270 allows the various fingers 144 and 146 to engage member 130 as described earlier in connection with FIG. 8. Tubes 270 and 380 can then be completely withdrawn from the patient, leaving the apparatus as shown in FIG. 23. The presence of clamp 140a pressing distally on the structure of proximal screw 150b may help to stiffen and strengthen distal anchor structure 110 (including screws 150a and 150b and spacer 160a). However, use of clamp 160a is optional.

Figure 24:
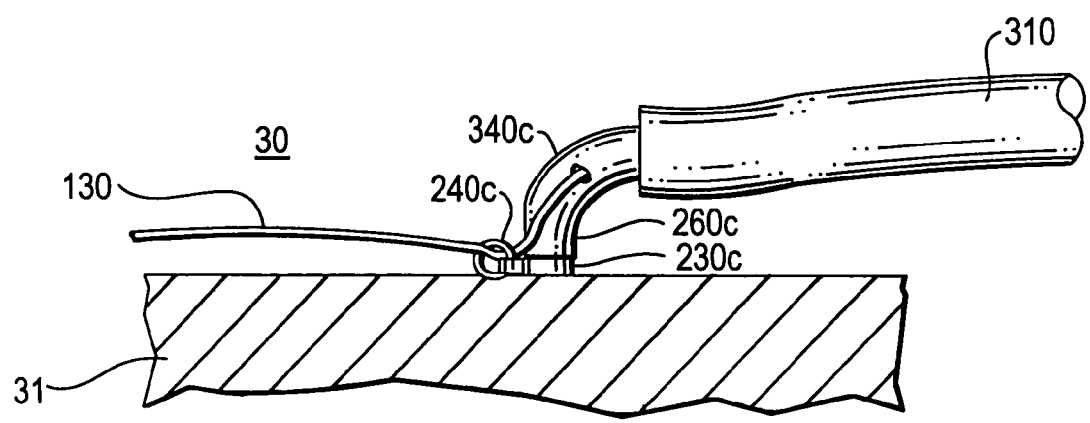
FIG. 24 is a simplified cross sectional view of another portion of what is shown in FIGS. 1, 9, and 10 at a particular intermediate stage in implanting a prosthesis in accordance with the invention.

The next step is to retract guide catheter 310 into the patient's right atrium 30 (see FIG. 24). The distal end of guide catheter 310 is placed near the desired location of third screw 150c. Delivery and implanting of third screw 150c can be similar (except for location) to delivery and implanting of second screw 150b. Accordingly, the description for third screw 150c can be somewhat abbreviated.

FIG. 24 shows the apparatus after the distal end of the delivery system for third screw 150c has been steered (deflected laterally) toward the desired implant site for screw 150c in the tissue 31 of right atrium 30. Once again, the above-mentioned Hindrichs et al. reference discusses preferred locations for a proximal tissue anchor. The proximal anchor placement principles discussed there are equally applicable to placing screw 150c in accordance with this invention. Those principles are preferably followed in locating and implanting screw 150c (and screw 150d) in practicing the present invention. As shown in FIG. 24, delivery system components 340c and 260c for third screw 150c position the collar 230c for the third screw against the surface of heart tissue 31 at the desired location. Linking member 130 comes from above-described distal anchor 110 (out of sight to the left in FIG. 24), passes through the ring 240c on collar 230c, and enters tubular member 340c.

If desired, the steering deflection of tubular member 340c can be passive deflection (i.e., a shape that is remembered by member 340c once that member is out of guide catheter 310). In coronary sinus 40 pull wires may be needed to generate more deflecting force and deform the coronary sinus. But in right atrium 30 tissue deformation may not be involved, and so passive steering deflection of tubular member 340c may be sufficient. (The same may be true for tubular member 340d, described below.)

Figure 25:
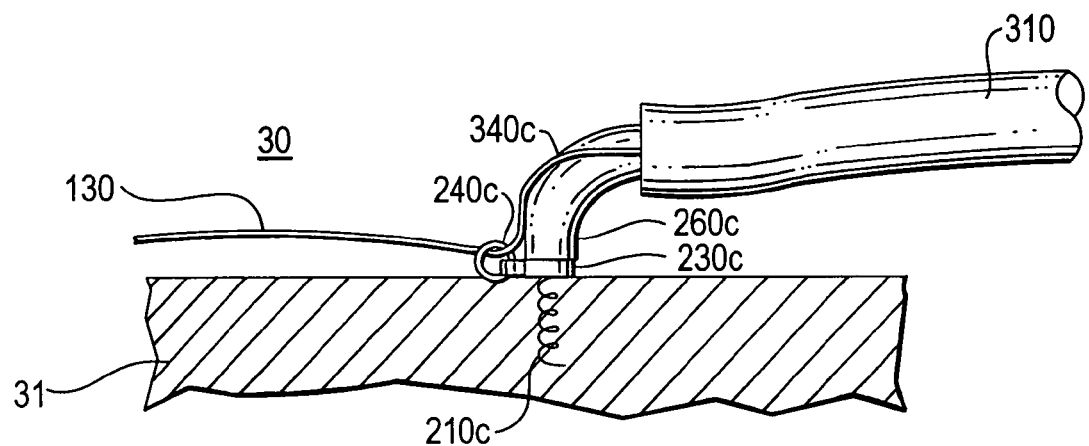
FIGS. 25-32 are similar to FIG. 24, but show successive, more subsequent stages in implanting a prosthesis in accordance with the invention.
Figure 26:
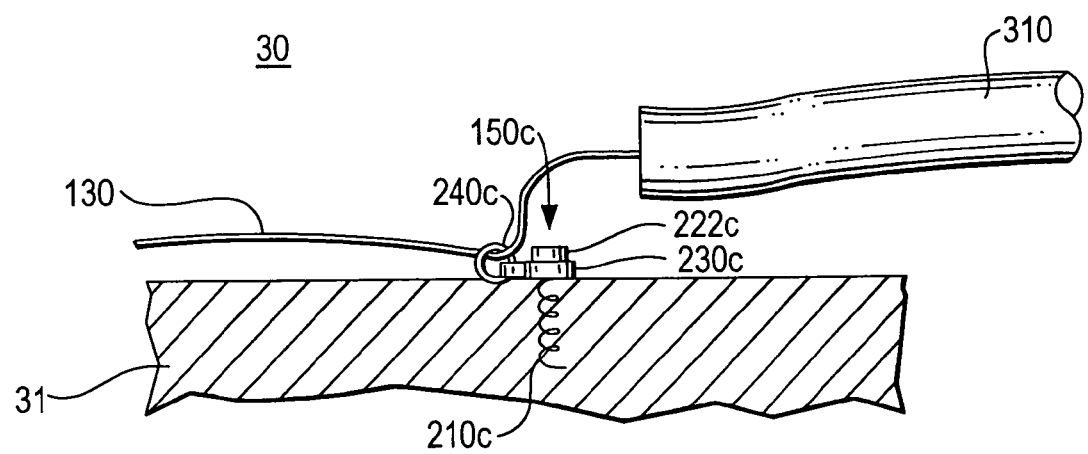

After collar 230c has been positioned as desired, the threaded portion 210c of that screw is driven (by other delivery system components that are inside components 340c and 260c and that are similar to components 350 and 250 (FIG. 14)) through collar 230c and into tissue 31 as shown in FIG. 25. Threaded portion 210c is then released from its holder/driver, collar 230c is released from its holder 260c, and the delivery system for screw 150c is re-straightened and withdrawn from the patient via guide catheter 310. The condition of the apparatus is now as shown in FIG. 26.

The next step is to insert spacer 160b into the patient along linking member 130 until it abuts the proximal side of screw 150c. This step is so similar to the insertion of spacer 160a that it does not need to be separately illustrated or further described.

Figure 27:
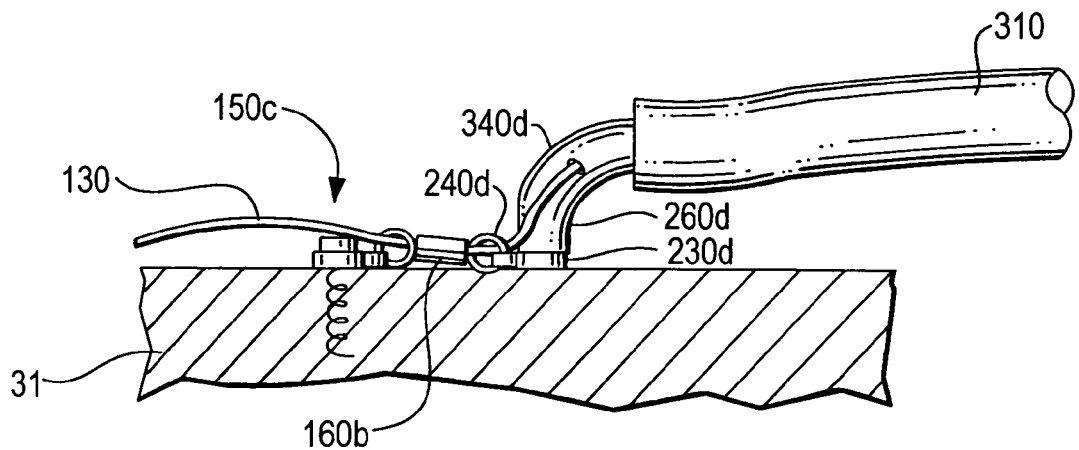

The next step is to reposition the distal end of guide catheter 310 for implanting of fourth screw 150d. Then the fourth screw and its delivery system are inserted into guide catheter 310 over linking member 130. The distal end of the delivery system 340d for fourth screw 150d is then steered toward tissue 31 just proximal to screw 150c and spacer 160b as shown in FIG. 27. Again, this steering may be passive as in the case of delivery system 340c.

Figure 28:
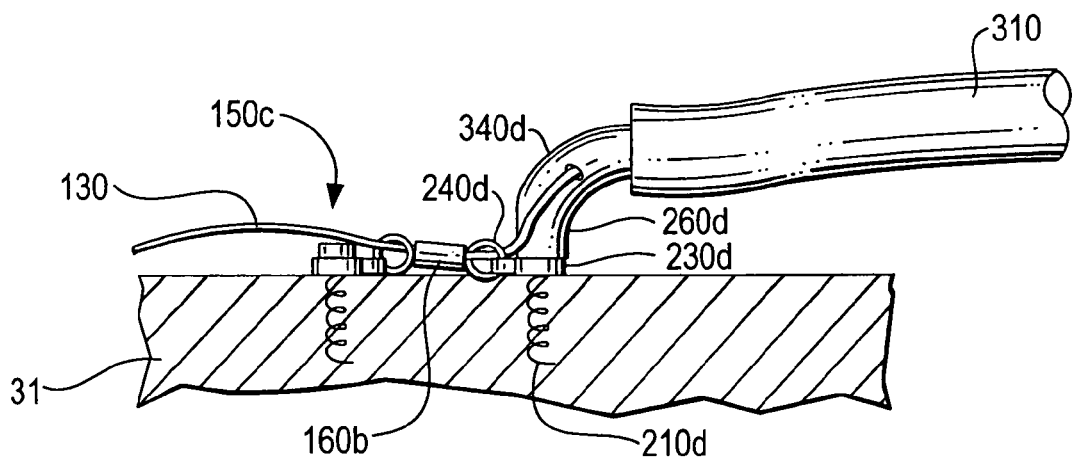
Figure 29:
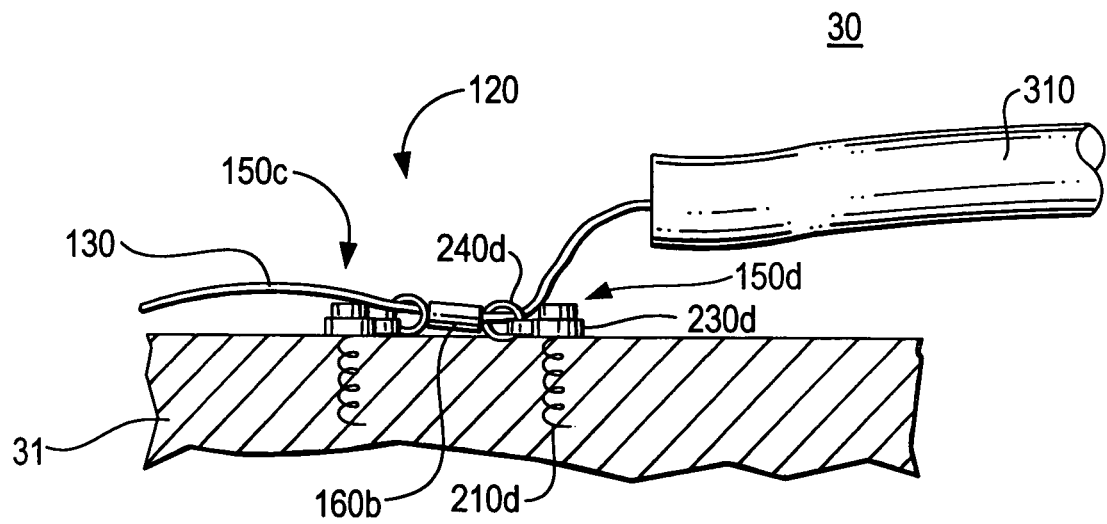

The next step, illustrated by FIG. 28, is to drive the threaded portion 210d of screw 150d through collar 230d and into tissue 31. Thereafter, threaded portion 210d is released from its holder/driver apparatus (not visible, but similar to previously shown and described components of the same kind), and collar 230d is released from its holder 260d. Delivery system 340d is then re-straightened and withdrawn from the patient via guide catheter 310. The condition of the apparatus is now as shown in FIG. 29.

Figure 30:
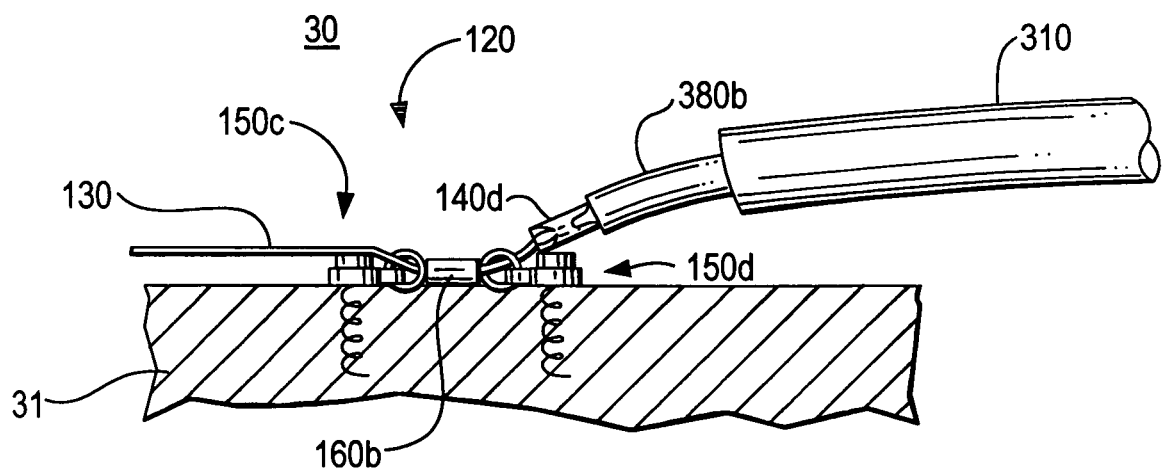

The next step is to introduce a second clamp 140b into the patient on second clamp delivery apparatus 380b (see FIG. 30). This is again done via guide catheter 310 and with all of elements 380b and 140b around the portion of linking member 130 that is proximal to proximal anchor structure 120. When clamp 140b reaches proximal anchor structure 120, linking structure 130 and structure 140b/380b can be used to shorten the distance between anchor structures 110 and 120 to any desired degree. This can be done by pulling proximally on the proximal end of linking structure 130 (outside of the patient) while pushing distally on components 140b/380b (also from outside the patient).

Figure 31:
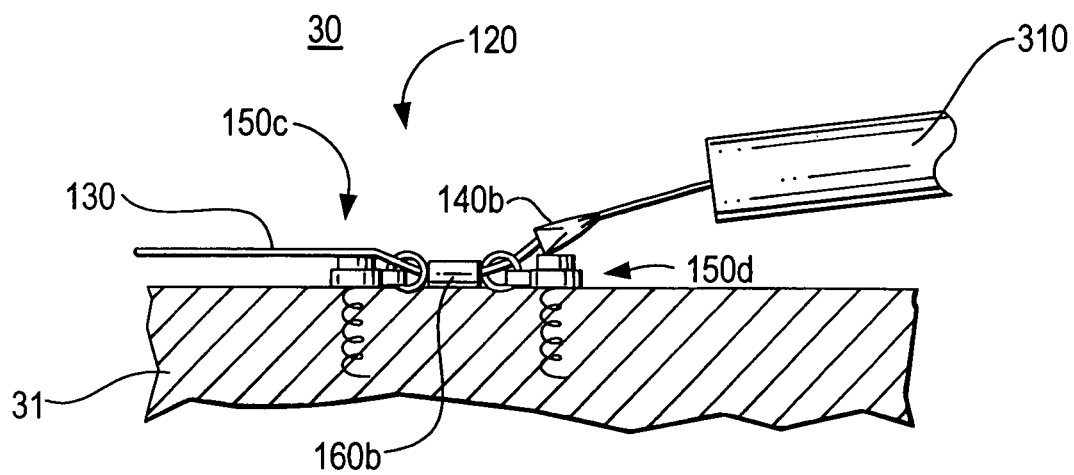

When the desired reduced spacing between anchor structures 110 and 120 has been achieved, the tube 270 (FIG. 7) on which clamp 140b is mounted is pulled proximally (while maintaining the relative positions of elements 130 and 140b/380b). This allows clamp 140b to grip linking member 130 and thereby fix the desired spacing between anchor structures 110 and 120. The externally applied tension on linking member 130 and compression on structure 380b can therefore be released, and the delivery apparatus for clamp 140b can be withdrawn from the patient. The condition of the apparatus is now as shown in FIG. 31.

It should be noted that the amount of spacing between distal and proximal anchor structures 110 and 120 is adjustable in both directions until clamp 140b is launched. This means that different spacings can be tried until the best spacing is found. Even if the spacing is initially decreased too much, that can be reversed by allowing the spacing to increase again. Clamp 140b is launched only after the best spacing has been found. It should also be noted that in this embodiment the spacing between anchor structures 110 and 120 is "infinitely adjustable" (within, of course, the practical range for such spacing). This means that within the practical range, the prosthesis can select and maintain any desired spacing between anchor structures 110 and 120.

The preceding paragraph refers to the possibility of trying different spacings of anchor structures 110 and 120 until the best spacing is found. The best spacing may be judged with the aid of any of a number of techniques such as direct visualization, fluoroscopy, echo cardiography, computed tomography, MRI, hemodynamic monitoring techniques, etc.

Figure 32:
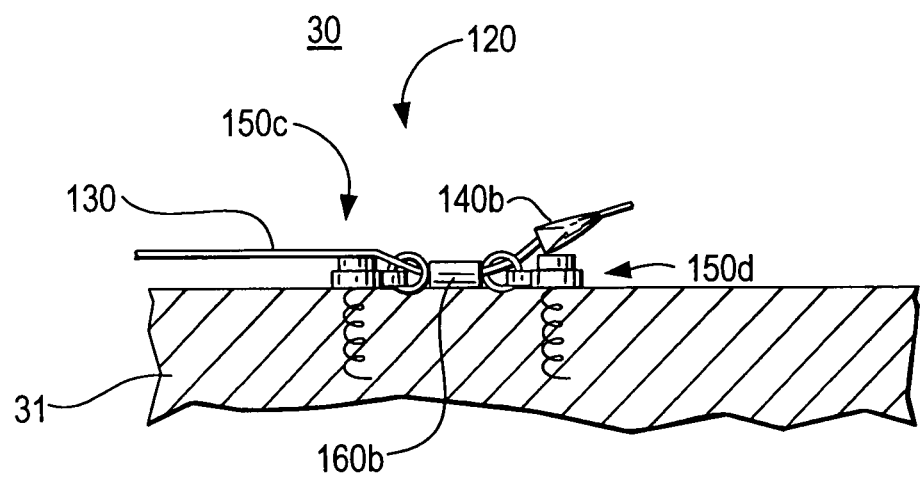

After clamp 140b has been launched, the next step is to cut linking structure 130 proximal to clamp 140b and to remove everything that is proximal to the cut. The condition of the apparatus is now as shown in FIG. 32 (and also FIG. 1). The process of implanting the prosthesis is complete and all delivery apparatus can be withdrawn from the patient.

A possible variation on the above method is to install the prosthesis as described above with little or no significant shortening of the distance between anchor structures 110 and 120. In this case the prosthesis acts as a precaution or prophylactic against possible future weakening and distension of the mitral valve annulus in the portion of that annulus that is spanned by the prosthesis.

Figure 34:
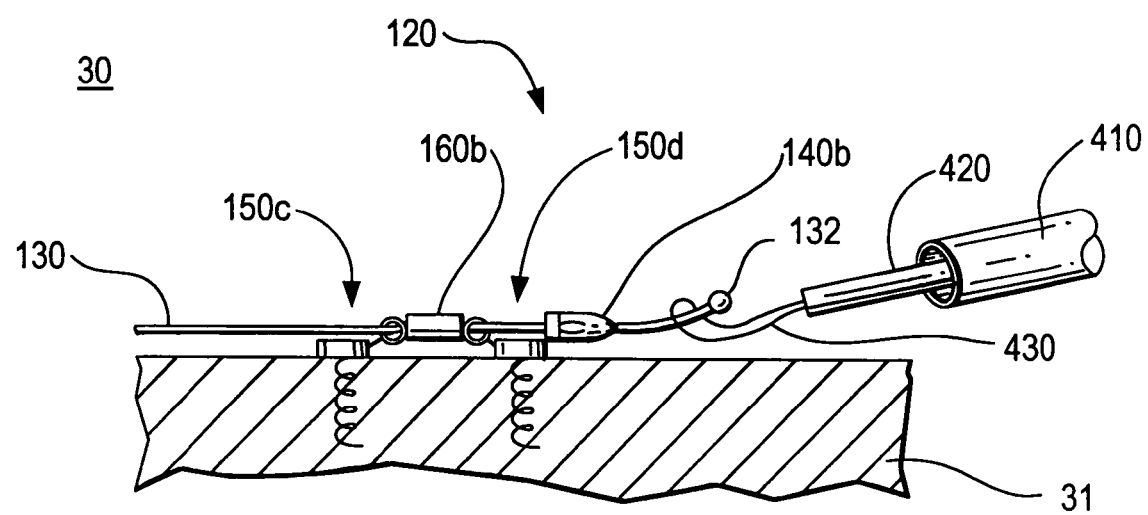
FIG. 34 is similar to FIG. 32, but shows another illustrative embodiment of the invention.

Another possible variation on the above-described methods and apparatus is illustrated by FIG. 34. In this embodiment the prosthesis is implanted as described above (with or without shortening of the distance between anchor structures 110 and 120). Some of linking member 130 is left proximal to clamp 140b. At any time after the prosthesis has been implanted in the patient (e.g., several weeks, months, or even years after implanting of the prosthesis), the patient can be re-entered to change or further change the spacing between anchor structures 110 and 120. As shown in FIG. 34, the re-entry apparatus may include catheter 410, which can be introduced into the patient percutaneously in the same way that other apparatus described above can be introduced. Catheter 410 is used to deliver snare structure 420/430 into the patient adjacent to the proximal end of linking member 130. Snare loop 430 is deployed and snares the proximal end of linking member 130. Linking member 130 may have been left with a proximal enlargement 132 to facilitate good engagement by snare loop 430. Enlargement 132 may be radio-opaque to facilitate finding it in the patient. Snare loop 430 is used to hold the end of linking structure 130 while snare tube 420 is pushed distally onto linking structure 130. When the distal end of snare tube 420 reaches clamp 160b, snare tube 420 can be used to push that clamp distally along linking member 130, while snare loop 430 is pulled proximally to hold linking member 130 in place. In this way the distance between anchor structures 110 and 120 can be shortened or further shortened at any time after the prosthesis has been implanted. When the desired shortening or further shortening has been achieved, linking member 130 can be released from snare loop 430 and apparatus 410/420/430 can be withdrawn from the patient. Clamp 140b will maintain the prosthesis with whatever spacing has been set between anchor structures 110 and 120.

Embodiments of the type illustrated by FIG. 34 may be desirable because they can take advantage of the fact that anchor structures 110 and 120 tend to be stronger after the tissue in which they are implanted has healed. For example, the prosthesis can be initially implanted with little or no shortening of the distance between anchor structures 110 and 120, and therefore with little or no tension in linking member 130. There is therefore little or no force acting on the anchor structures that might tend to pull them from the tissue. After the tissue has healed, the anchor structures are stronger than they are when first implanted. The technique and apparatus illustrated by FIG. 34 can then be used to tension linking member 130 and shorten the distance between anchor structures 110 and 120. Because the tissue at the anchor structures has already healed when this is done, the prosthesis is even more secure than it otherwise would have been.

It will be understood that the foregoing is only illustrative of the principles of the invention, and that various modifications can be made by those skilled in the art without departing from the scope and spirit of the invention. For example, use of clamp structure 140*a* (FIGS. 22 and 23) is optional, and that structure can be omitted from the prosthesis if desired. As another example of a possible modification, each screw 210 could be held on its holder 250 by structures 254 (FIG. 3) that are resiliently biased to deflect outwardly rather than inwardly as described above. Each ring 240 (e.g., FIG. 2) could be integrated into the associated collar 230 rather than being a separate component. Each of anchor structures 110 and 120 could be on a separate linking member like 130, with both of those linking members pulled through a common final clamp (like 140*b*) to pull the two anchor structures together. The above-mentioned Hindrichs et al. reference shows this type of use of two strands pulled through a common final clamp. One or more of anchor structures 110 and 120 can be (or can include) a tissue-piercing lead for any type of electrical apparatus. Linking member 130 can be or can be part of an electrical conductor that is electrically connected to the tissue-piercing lead. This conductor can extend to other electrical apparatus inside and/or outside the patient. Any portion or portions of the prosthesis can have one or more coatings for biological purposes such as to reduce inflammatory response, promote healing, reduce clotting or thrombogenicity response, etc. For example, this may be accomplished by using one or more polymer coatings that can elute one or more drugs or medications. Linking member 130 can have radio-opaque markers at predetermined spacings or locations to help visualize the amount of shortening between an chor structures 110 and 120 that is being achieved. Any of the materials and/or material constructions mentioned anywhere throughout this specification can be used for any component or components of the prosthesis, as is appropriate for that component or for those components.

As is mentioned earlier in this specification, screw structures 150 of the types shown and described herein have features that may permit effective use of only one such screw (rather than a pair) as an anchor structure such as 110 and/or 120 in a prosthesis in accordance with this invention. For example, collar 230 may act as a washer that bears on the surface of tissue and helps to reduce tipping of a single screw structure 150 when that structure is pulled on by the linking member 130 of a prosthesis. Similarly, the fact that the point of attachment of linking member 130 to screw structure 150 is on collar 230 (which is at or close to the tissue surface rather than at the top of the screw structure) and off the central longitudinal axis of screw structure 150 may further help to reduce tipping of a single screw structure when pulled by the linking member. As is explained earlier in this specification, a screw that can remain transverse to the direction of pull tends to resist pulling out of tissue better than a screw that can tip over and become aligned with the direction of pull. Thus the above-mentioned features that help even a single screw structure of this invention resist tipping over make such a screw structure a better, stronger anchor structure even when used alone and without a second screw in a tandem pair.

Although the invention has been illustrated for the most part in the context of percutaneous mitral valve repair, it has also been mentioned that aspects of the invention are alternatively usable non-percutaneously and/or for other types of prostheses. The above-mentioned Hindrichs et al. reference shows and describes several examples of such other contexts, and it will be apparent from what has been said above how features of the present invention can be employed in those contexts.

The invention claimed is:

1. A prosthesis for reducing distance between first and second portions of soft body tissue structure comprising:
   a first anchor structure for inserting into soft tissue, the first anchor structure including first and second screw structures threaded into the first portion of the tissue structure with a first substantially rigid spacer structure for maintaining a space between the first and second screw structures, one of the first and second screw structures including a hollow, helical screw portion, a hollow head portion forming a hollow cylinder with a flange extending radially from a proximal end of the cylinder, and an annular collar fitted around an outside of the head portion so that the screw structure is rotatable about a longitudinal axis relative to the collar, the flange being too large to pass through the collar;
   a second anchor structure for inserting into soft tissue, the second anchor structure including third and fourth screw structures threaded into the second portion of the tissue structure with a second substantially rigid spacer structure for maintaining a space between the third and fourth screw structures; and
   linking structure between the first and second anchor structures,
   wherein the first and second screw structures are located along a first axis defined by the linking structure and the third and fourth screw structures are located along a second axis defined by the linking structure, and the space between the first and second screw structures is approximately equal to a length of the first substantially rigid spacer structure and the space between the third and fourth screw structures is approximately equal to a length of the second substantially rigid spacer structure, and wherein the head portion includes a plurality of T-shaped recesses that receive portions of a screw driving apparatus to releasably hold the screw portion on the screw driving apparatus, the T-shaped recesses having a wider portion positioned proximate the hollow helical screw portion, the T-shaped recesses being longitudinally aligned with the hollow head portion, the T-shaped recesses being spaced around a circumference of the hollow head portion, and the T-shaped recesses being accessible from a hollow interior of the hollow head portion.

2. The prosthesis defined in claim 1 wherein the first and second screw structures are threaded into the first portion of the tissue structure transverse to a longitudinal axis of an adjacent portion of the linking structure.

3. The prosthesis defined in claim 2 wherein the third and fourth screw structures are threaded into the second portion of the tissue structure transverse to a longitudinal axis of an adjacent portion of the linking structure.

4. The prosthesis defined in claim 1 further comprising means for maintaining a selectable length of the linking structure between the first and second anchor structures.

5. The prosthesis defined in claim 4 wherein the means for maintaining comprises:
a clamp structure for selectively clamping onto the linking structure.

6. The prosthesis defined in claim 5 wherein the clamp structure clamps the linking structure adjacent to the fourth screw structure.

7. The prosthesis defined in claim 4 wherein the means for maintaining is deployable to select and maintain any length of the linking structure between the first and second anchor structures within a range of such lengths.

8. The prosthesis defined in claim 7 wherein the means for maintaining has a pre-deployment state in which it permits the length of the linking structure between the first and second anchor structures to be increased or decreased.

9. The prosthesis defined in claim 1 wherein the head portion traps the collar against tissue into which the screw portion is threaded.

10. The prosthesis defined in claim 9 wherein the collar includes structure for engaging the linking structure.

11. The prosthesis defined in claim 10 wherein the structure for engaging holds the collar at a fixed location on the linking structure.

12. The prosthesis defined in claim 10 wherein the structure for engaging allows the collar to slide along the linking structure.

13. The prosthesis of claim 10, wherein the structure for engaging the linking structure is a capturing ring and the linking structure passes loosely through the ring.

14. The prosthesis defined in claim 1 wherein the first substantially rigid spacer structure is slidable along the linking structure.

15. The prosthesis defined in claim 14 wherein the second substantially rigid spacer structure is slidable along the linking member.

16. The prosthesis defined in claim 1 wherein the linking structure is flexible.

17. The prosthesis of claim 1, wherein the linking structure passes through an eyelet on at least one screw structure.

18. The prosthesis of claim 1, wherein the liking structure includes a proximal enlargement.

19. The prosthesis of claim 18, wherein the proximal enlargement is radio-opaque.

20. The prosthesis of claim 1, wherein the linking structure includes one or more radio-opaque markers.

21. The prosthesis of claim 1, wherein the linking structure forms part of an electrical conductor.

22. The prosthesis of claim 1, wherein the one of the first and second screw structures includes a sharply pointed distal tip, a plurality of helical turns that connect the distal tip to the head portion, the plurality of helical turns having at least one anticlinal barb to resist unthreading of the screw structure from tissue.

23. The prosthesis of claim 1, wherein the collar comprises a plurality of recesses for releasably securing the collar to an implanting apparatus.

24. The prosthesis of claim 1, further comprising the screw driving apparatus, the screw driving apparatus including a hollow cylindrical proximal portion and a plurality of distally extending T-shaped portions that are sized and shaped to fit into the T-shaped recesses, the T-shaped portions being resiliently biased to deflect inwardly, towards one another.

25. The prosthesis of claim 24, further comprising a collar holder, the collar holder including a hollow cylindrical proximal portion and a plurality of distally extending fingers, wherein the hollow cylindrical proximal portion fits concentrically around the screw driving apparatus.

26. A prosthesis for adjusting a distance between a first portion and a second portion of soft body tissue, the prosthesis comprising:
a first anchor assembly for inserting into soft tissue, the first anchor assembly including a first pair of spaced apart rotatable tissue screws having hollow, helical threads and arranged for rotatable insertion into the first portion of soft body tissue, a hollow head portion forming a hollow cylinder with flange extending radially from a proximal end of the cylinder, and an annular collar fitted around an outside of the head portion so that the screw structure is rotatable about a longitudinal axis relative to the collar, the flange being too large to pass through the collar;
a second anchor assembly for inserting into soft tissue, the second anchor assembly including a second pair of spaced apart rotatable tissue screws having helical threads and arranged for rotatable insertion into the second portion of soft body tissue;
a first spacer disposed between the first pair of rotatable tissue screws and a second spacer disposed between the second pair of rotatable tissue screws, the first and second spacers comprising substantially rigid hollow cylinders; and
a tensionable link, the link extending between and coupling the first anchor assembly and the second anchor assembly, the link further extending between the first pair of spaced apart rotatable tissue screws through the first spacer, and between the second pair of rotatable tissue screws through the second spacer,
wherein the first pair of spaced apart rotatable tissue screws lie along a first axis defined by the tensionable link, and the second pair of spaced apart rotatable tissue screws lie along a second axis defined by the tensionable link, and
wherein the hollow head portion includes a plurality of T-shaped recesses that receive portions of a screw driving apparatus to releasably hold the tissue screws on the screw driving apparatus, the T-shaped recesses having a wider portion positioned proximate the hollow helical threads, the T-shaped recesses being longitudinally aligned with the hollow head portion, the T-shaped recesses being spaced around a circumference of the hollow head portion, and the T-shaped recesses being accessible from a hollow interior of the hollow head portion.

27. The prosthesis of claim 26, including a clamp coupled to the tensionable link at a selected location and arranged to maintain a desired spacing between the first anchor assembly and the second anchor assembly.

28. The prosthesis of claim 26, wherein the link is flexible, and wherein each of the first and second spacers surrounds a corresponding portion of the link, and further wherein each of the first and second spacers is sized to abut both of the adjacent rotatable tissue screws when the link is tensioned.

* * * * *